United States Patent
Carrió et al.

(10) Patent No.: US 12,129,280 B2
(45) Date of Patent: *Oct. 29, 2024

(54) ONCOLYTIC ADENOVIRUSES FOR TREATING CANCER

(71) Applicants: Fundació Institut D'Investigació Biomèdica De Bellvitge (IDIBELL), Barcelona (ES); INSTITUT CATALA. D'ONCOLOGIA, Barcelona (ES)

(72) Inventors: Sònia Guedan Carrió, Manresa (ES); Manel Maria Cascallo Piqueras, Gelida (ES); Ramon Alemany Bonastre, Castelldefels (ES)

(73) Assignees: FUNDACIÓ INSTITUT D'INVESTIGACIÓ BIOMEDICA DE BELLVITGE, Barcelona (ES); INSTITUT CATALA D'ONCOLOGIA, Barcelona (ES)

( * ) Notice: Subject to any disclaimer, the term of this patent is extended or adjusted under 35 U.S.C. 154(b) by 478 days.

This patent is subject to a terminal disclaimer.

(21) Appl. No.: 16/405,285

(22) Filed: May 7, 2019

(65) Prior Publication Data

US 2019/0345204 A1 Nov. 14, 2019

Related U.S. Application Data

(63) Continuation of application No. 13/318,876, filed as application No. PCT/ES2010/000196 on May 5, 2010, now Pat. No. 10,316,065.

(30) Foreign Application Priority Data

May 6, 2009 (ES) .................................. 200901201

(51) Int. Cl.
| | | |
|---|---|---|
| *A61K 35/761* | (2015.01) | |
| *A61K 38/00* | (2006.01) | |
| *C07K 5/00* | (2006.01) | |
| *C07K 14/005* | (2006.01) | |
| *C12N 7/00* | (2006.01) | |
| *C12N 9/24* | (2006.01) | |
| *C12N 9/26* | (2006.01) | |
| *C12N 15/86* | (2006.01) | |
| *C12N 15/861* | (2006.01) | |

(52) U.S. Cl.
CPC .......... *C07K 14/005* (2013.01); *A61K 35/761* (2013.01); *C12N 7/00* (2013.01); *C12N 9/2474* (2013.01); *C12N 15/86* (2013.01); *A61K 38/00* (2013.01); *C12N 2710/10321* (2013.01); *C12N 2710/10322* (2013.01); *C12N 2710/10332* (2013.01); *C12N 2710/10343* (2013.01); *C12N 2710/10371* (2013.01)

(58) Field of Classification Search
None
See application file for complete search history.

(56) References Cited

U.S. PATENT DOCUMENTS

| | | |
|---|---|---|
| 5,516,631 A | 5/1996 | Frisch |
| 5,677,178 A | 10/1997 | McCormick |
| 5,721,348 A | 2/1998 | Primakoff |
| 5,801,029 A | 9/1998 | McCormick |
| 5,885,808 A | 3/1999 | Spooner et al. |
| 5,972,706 A | 10/1999 | McCormick |
| 5,998,205 A | 12/1999 | Hallenbeck et al. |
| 6,197,754 B1 | 3/2001 | Hung et al. |
| 6,495,130 B1 | 12/2002 | Henderson et al. |
| 6,551,587 B2 | 4/2003 | Hallenbeck et al. |
| 6,692,956 B2 | 2/2004 | Rooke |
| 6,824,771 B1 | 11/2004 | Curiel et al. |
| 7,001,596 B1 | 2/2006 | Leisa et al. |
| 7,078,030 B2 | 7/2006 | Johnson et al. |
| 7,109,029 B2 | 9/2006 | Clarke et al. |
| 7,253,150 B1 | 8/2007 | Noteborn |
| 7,261,885 B2 | 8/2007 | Falck-Pedersen et al. |
| 7,297,542 B2 | 11/2007 | Curiel et al. |
| 7,767,429 B2 | 8/2010 | Bookbinder et al. |
| 7,807,618 B2 | 10/2010 | Matalon |
| 7,902,441 B2 | 3/2011 | Ji et al. |
| 10,316,065 B2 * | 6/2019 | Carrió .................... C12N 15/86 |
| 2002/0037274 A1 | 3/2002 | Williams et al. |
| 2003/0104625 A1 | 6/2003 | Cheng et al. |

(Continued)

FOREIGN PATENT DOCUMENTS

| | | |
|---|---|---|
| EP | 0 445 939 | 9/1991 |
| WO | 94/18992 | 9/1994 |

(Continued)

OTHER PUBLICATIONS

Fumoto et al, Targeted Gene Delivery: Importance of Administration Routes, INTECH, 2013, pp. 3-31.*
Kaufman et al, Oncolytic viruses: a new class of immunotherapy drugs, Nature, 2015, pp. 642-662.*
Russell et al, Oncolytic Virotherapy, 2014, Nat Biotechnol.; 30(7): pp. 1-31.*

(Continued)

*Primary Examiner* — Maria Marvich

(74) *Attorney, Agent, or Firm* — Morgan, Lewis & Bockius LLP

(57) ABSTRACT

The invention is related to an oncolytic adenovirus that comprises a sequence encoding a hyaluronidase enzyme inserted in its genome. This adenovirus spreads more efficiently in the tumour mass and therefore the oncolytic effect is increased. Injecting the oncolytic adenovirus of the invention endovenously, tumour volume regressions are obtained. Therefore the oncolytic adenovirus of the present invention is useful for the treatment of a cancer or a pre-malignant state of cancer.

18 Claims, 12 Drawing Sheets

Specification includes a Sequence Listing.

(56) References Cited

U.S. PATENT DOCUMENTS

| | | |
|---|---|---|
| 2003/0215432 A1 | 11/2003 | Matalon |
| 2003/0215948 A1 | 11/2003 | Kaleko et al. |
| 2004/0048821 A1 | 3/2004 | Lowe |
| 2006/0147420 A1 | 7/2006 | Fueyo |
| 2006/0292682 A1 | 12/2006 | Hawkins et al. |
| 2007/0036721 A1 | 2/2007 | Zinn |
| 2007/0092968 A1 | 4/2007 | Ji et al. |
| 2007/0172846 A1 | 7/2007 | Zhang et al. |
| 2008/0124360 A1 | 5/2008 | Seggern |
| 2008/0171390 A1 | 7/2008 | Yu et al. |
| 2009/0180994 A1 | 7/2009 | Groene et al. |
| 2009/0311664 A1 | 12/2009 | Fong et al. |
| 2010/0105122 A1 | 4/2010 | Thompson et al. |
| 2011/0053247 A1 | 3/2011 | Baker et al. |
| 2019/0241877 A1* | 8/2019 | DeKelver ...... C12Y 304/21022 |

FOREIGN PATENT DOCUMENTS

| | | |
|---|---|---|
| WO | 96/03151 | 2/1996 |
| WO | 00/22137 | 4/2000 |
| WO | 0029599 | 5/2000 |
| WO | 2004078140 | 9/2004 |
| WO | 2005/018332 | 3/2005 |
| WO | 2006091871 | 8/2006 |

OTHER PUBLICATIONS

Ferguson et al, Systemic Delivery of Oncolytic Viruses: Hopes and Hurdles, Advances in Virology vol. 2012, pp. 1-14.*

He et al, Extracellular matrix in cancer progression and therapy, Med. Rev. 2022; 2(2): 125-139.*

Zhao et al, Oncolytic Adenovirus: Prospects for Cancer Immunotherapy, Frontiers in Microbiology, 2021, pp. 1-16.*

Ji et al, Strategies for Advanced Oncolytic Virotherapy: Current Technology Innovations and Clinical Approaches, Pharmaceutics 2022, pp. 1-23.*

Oronsky et al, Oncolytic adenoviruses: The Cold War against Cancer Finally Turns Hot, Cancers, 2022, pp. 1-13.*

Bayo-Puxan et al, Replacement of Adenovirus Type 5 Fiber Shaft Heparan Sulfate Proteoglycan-Binding Domain with RGD for Improved Tumor Infectivity and Targeting, Human Gene Therapy 20:1214-1221 (Oct. 2009).*

McKenna et al, Modeling the Efficacy of Oncolytic Adenoviruses In Vitro and In Vivo: Current and Future Perspectives, Cancers 2020, pp. 1-17.*

Liao et al, Potential targeting of the tumor microenvironment to improve cancer virotherapy, Pharmacology & Therapeutics 250 (2023), pp. 1-11.*

Jung et al, In vivo estimation of oncolytic virus populations within tumors, Cancer Res. Oct. 15, 2018; 78(20): 5992-6000.*

Vähä-Koskela and Hinkkanen, Tumor Restrictions to Oncolytic Virus, Biomedicines 2014, 2, 163-194.*

Shanks et al, Are animal models predictive for humans? Philosophy, Ethics, and Humanities in Medicine, 2009, pp. 1-20.*

Martinez et al, Oncolytic viruses: overcoming translational challenges, J Clin Invest. 2019; 129(4):1407-1418.*

Bauerschmitz et al. "Evaluation of a Selectively Oncolytic Adenovirus for Local and Systemic Treatment of Cervical Cancer" Int. J. Cancer (2004), 111, 303-309.

Bernt et al. "Assessment of a Combined, Adenovirus-Mediated Oncolytic and Immunostimulatory Tumor Therapy" Cancer Res (2005) 65(10), 4343-4352.

Demers et al. "Pharmacologic Indicators of Antitumor Efficacy for Oncolytic Virotherapy" Cancer Research (2003) 63, 4003-4008.

Fuerer et al. "5-Fluorocytosine increases the toxicity of Wnt-targeting replicating adenoviruses that express cytosine deaminase as a late gene" Gene Therapy (2004), 11, 142-151.

Kirn et al "Clinical research results with dl1520 (Onyx-015), a replication-selective adenovirus for the treatment of cancer: what have we learned?" Gene Therapy (2001), 8, 89-98.

Lyons et al. "Adenovirus Type 5 Interactions with Human Blood Cells May Compromise Systemic Delivery" Molecular Therapy (2006), 14(1), 118-128.

Nemunaitis et al. "A phase I trial of intravenous infusion of ONYX-015 and enbrel in solid tumor patients" Cancer Gene Therapy (2007), 14, 885-893.

Quirin et al. "Selectivity and Efficiency of Late Transgene Expression by Transcriptionally Targeted Oncolytic Adenoviruses are Dependent on the Transgene Insertion Strategy" Human Gene Therapy (2011), 22, 389-404.

Stern "Hyaluronan metabolism: a major paradox in cancer biology" Pathologie Biologie (2005), 53, 372-382.

Villanueva et al. "Codon optimization of the adenoviral fiber negatively impacts structural protein expression and viral fitness" Scientific Reports (2016) 6:27546.

Shen, Z., "Anthropotomy and Histoembryology", Aug. 2006, p. 16, Publisher: Shanghai Scientific and Technical Publishers.

Shen, Z., "Anthropotomy and Histoembryology", Aug. 2006, p. 16, Eng Trans, Publisher: Shanghai Scientific and Technical Publishers.

Zhang, Y., et al., "Medical Enzymology and Clinic", May 1996, p. 173, Publisher: China Science and Technology Press.

Zhang, Y., et al., "Medical Enzymology and Clinic", May 1996, p. 173, Eng Trans, Publisher: China Science and Technology Press.

Bauzon and Hermiston. "Exploiting diversity: Genetic approaches to creating highly potent and efficacious oncolytic viruses" 2008. Current Opinion in Molecular Therapeutics, 10(4):350-355.

Belousova et al. "Modification of Adenovirus Capsid with a Designed Protein Ligand Yields a Gene Vector Targeted to a Major Molecular Marker of Cancer" 2008. Journal of Virology, 82(2):630-637.

Choi et al. "Intraperitoneal Immunotherapy for Metastic Ovarian Carcinoma: Resitance of Intratumoral Collagen to Antibody Penetration" 2006. Clin Cancer Res, 12:1906-1912.

Chow et al. "Transformation of Rodent Fibroblasts by the Jaagsiekte Sheep Retrovirus Envelope is Receptor Independent and Does not Require the Surface Domain" 2003. Journal of Virology, 77(11):6341-6350.

Cody et al. "Armed replicating adenoviruses for cancer virotherapy" 2009. Cancer Gene Ther, 16(6): 473-488.

Conteduca et al. "Precancerous colorectal lesions (Review)" 2013. Int J Oncol. 43(4):973-84.

Database NCBI. Gene ID: 6677. SPAM1 sperm adhesion molecule 1 [Homo sapiens (human)].

Erikson et al. "The Impact of Enzymatic Degradation on the Uptake of Differently Sized Therapeutic Molecules" 2008. Anticancer Res, 28:3557-66.

"Frost. ""Recombinant human hyaluronidase (rHuPH20): an enabling platform forsubcutaneous drug and fluid administration"" 2007. Exper Opin Drug Deliv, 4(4): 1-14.".

"Fuerer and Iggo. ""5-Fluorocytosine increases the toxicity of Wnt-targeting replicating adenoviruses that expresscytosine deaminase as a late gene"" 2004. Gene Therapy, 11, 142-151.".

Glasgow et al. "Transductional targeting of adenovirus vectors for gene therapy" 2006. Cancer Gene Therapy, 13(9):830-844.

Haisma et al. "Targeting of adenoviral vectors through a bispecific single-chain antibody" 2000. Cancer Gene Therapy, 7(6):901-904.

Han et al. "Genetic incorporation of the protein transduction domain of Tat into Ad5 fiber enhances gene transfer efficacy" 2007. Virology Journal, 4:103.

Haseley et al. "Advances in Oncolytic Virus Therapy for Glioma" 2009. Recent Pat CNS Drug Discov, 4(1):1-13.

Hawkins et al. "Gene delivery from the E3 region of replicating human adenovirus: evaluation of the 6.7 K/gp19 K region" 2001. Gene Therapy, 8(15):1123-31.

Hleise et al. "An adenovirus E1A mutant that demonstrates potent and selective systemic anti-tumoral efficacy" 2000. Nature Medicine, 6(10):1134-1139.

Holland-Frei Cancer Medicine. 6th edition. Kufe DW et al., editors. Hamilton (ON): BC Decker; 2003. Part III. Cancer Diagnosis. Section 6: Cancer Pathology. Principles of cancer Pathology. Tumor stroma generation; available online Chapter 35: http://www.ncbi.nlm.nih.gov/books/bv.fcgi?rid=cmed6.section.8164).

(56) References Cited

OTHER PUBLICATIONS

Ji et al. 2002. "Expression of Several Genes in the Human Chromosome 3p21.3 Homozygous Deletion Region by an Adenovirus Vector Results in Tumor Suppressor Activities in Vitro and in Vivo" Cancer Res, 62:2715-2720.
Jung et al. "Retargeting of adenoviral gene delivery via Herceptin-PEG-adenovirusconjugates to breast cancer cells" 2007. Journal of Controlled Release, 123(2007):164-171.
Krasnykh et al. "Generation of Recombinant Adenovirus Vectors with Modified Fibers for Altering Viral Tropism" 1996. Journal of Virology, 70(10):6839-6846.
Kretschmer et al. "Development of a Transposon-Based Approach for Identifying Novel Transgene Insertion Sites within the Replicating Adenovirus" 2005. Molecular Therapy, 12(1):118-127.
Kumar et al. "Virus combinations and chemotherapy for the treatment of human cancers" 2008. Current Opinion in Molecular Therapeutics, 10(4):371-379.
Lichtenstein et al. "An acute toxicology study with INGN 007, an oncolytic adenovirus vector, in mice and permissive Syrian hamsters; comparisons with wild-type Ad5 and a replication-defective adenovirus vector" 2009. Cancer Gene Ther, 16(8):644-654.
Liu et al. "Clinical trial results with oncolytic virotherapy: a century of promise, a decade of progress" 2007. Nature Clinical Practice Oncology, 4(2):101-117.
Liu et al. "Oncolytic Adenoviruses for Cancer Gene Therapy" 2008. Methods in Molecular Biology, 433: 243-258.
Lokeshwar et al. "HYAL1 Hyaluronidase in Prostate Cancer: A Tumor Promoter and Suppressor" 2005. Cancer Res, 65:7782-9.
Nettelbeck. "Cellular genetic tools to control oncolytic adenoviruses for virotherapy of cancer" 2008. J. Mol. Med. 86, 363-377.
Noureddini and Curiel. "Genetic Targeting Strategies for Adenovirus" 2005. Molecular Pharmaceutics, 2(5):341-347.
Novak et al. "Hyaluronidase-2 Overexpression Accelerates Intracerebral but not Subcutaneous Tumor Formation of Murine Astrocytoma Cells" 1999. Cancer Res, 59:6246-6250.
Page et al. "Identifying the safety profile of a novel infectivity-enhanced conditionally replicative adenovirus, Ad5-24-RGD, in anticipation of a phase I trial for recurrent ovarian cancer" 2007. American Journal of Obstetrics & Gynecology, 196(4):389.e1-10.
Panwar et al. "Management for premalignant lesions of the oral cavity" 2014. Expert Rev Anticancer Ther. 14(3):349-57.
Quirin et al. "Selectivity and Efficiency of Late Transgene Expression by Transcriptionally Targeted Oncolytic Adenoviruses are Dependent on the Transgene Insertion Strategy" 2011. Human Gene Therapy, 22:389-404.
"Rein et al. ""Gene Transfer To Cervical Cancer With Fiber-Modifiedadenoviruses"" 2004. Int J Cancer, 111: 698-704.".
Robinson et al. "Comparison of the E3 and L3 regions for arming oncolytic adenoviruses to achieve a high level of tumor-specific transgene expression" 2008. Cancer Gene Ther. 15(1):9-17.
Rojas et al. "Improved systemic antitumor therapy with oncolytic adenoviruses by replacing the fiber shaft HSG-binding domain with RGD" 2011. Gene Therapy, (2011): 1-5.
Rooney and Kumar. "Inverse relationship between hyaluronan and collagens in development and angiogenesis" 1993. Differentiation, 54:1-9.
Shenk T. Adenoviridae: The viruses and their replication. Chaper 67. Fields Virology. Third Edition 1996. Lippincott-Raven Publishers.
Shuster et al. "Hyaluronidase Reduces Human Breast Cancer Xenografts in SCID Mice" 2002. Int J Cancer 102:192-197.
Stern and Jedrzejas. "The Hyaluronidases: Their Genomics, Structures, and Mechanisms of Action" 2006. Chem. Rev. 106(3):818-39.
Stern. "Hyaluronidases in cancer biology" 2008. Seminars in Cancer Biology, 18 (2008):275-280.
Suzuki et al. "Preferable sites and orientations of transgene inserted in the adenovirus vector genome: The E3 site may be unfavorable for transgene position" 2015. Gene Therapy, (2015): 1-9.
Toth et al. "An Oncolytic Adenovirus Vector Combining Enhanced Cell-to-Cell Spreading, Mediated by the ADP Cytolytic Protein, with Selective Replication in Cancer Cells with Deregulated Wnt Signaling" 2004. Cancer Research, 64:3638-3644.
Tufto et al. "The Effect of Collagenase and Hyaluronidase on Transient Perfusion in Human Osteosarcoma Xenografts Grown Orthotopically and in Dorsal Skinfold Chambers" 2007. Anticancer Res, 27:1475-81.
Unemori et al. "Relaxin Induces an Extracellular Matrix-degrading Phenotype in Human Lung Fibroblasts In Vitro and Inhibits Lung Fibrosis in a Murine Model In Vivo" 1996. J Clin Invest, 98: 2739-45.
Van Beusechem et al. "Efficient and Selective Gene Transfer into Primary Human Brain Tumors by Using Single-Chain Antibody-Targeted Adenoviral Vectors with Native Tropism Abolished" 2002. Journal of Virology, 76(6):2753-2762.
WHO Guidelines for Screening and Treatment of Precancerous Lesions for Cervical Cancer Prevention. Geneva: World Health Organization; 2013.
Wu and Curiel. 2008. From: Methods in Molecular Biology, vol. 434: vol. 2: Design and Characterization of Gene Transfer Vectors. Edited by: J. M. Le Doux, Humana Press, Totowa, NJ. pp. 113-132.
Yoon et al. "Targeting a Recombinant Adenovirus Vector to HCC Cells Using a Bifunctional Fab-Antibody Conjugate" 2000. Biochemical and Biophysical Research Communications, 272:497-504.
Rodriguez-Garcia et al. "Safety and Efficacy of VCN-01, an Oncolytic Adenovirus Combining Fiber HSG-Binding Domain Replacement with RGD and Hyaluronidase Expression" 2015. Clin Cancer Res, 21(6): 1406-1418.
Fukuhara et al. "Oncolytic Virus Therapy: A New Era of Cancer Treatment at Dawn" Cancer Sci, 107 (2016) 1373-1379.
Hiofinger et al. "Kinetics of Hyal-1 and PH-20 Hyaluronidases: Comparison of Minimal Substrates and Analysis of the Transglycosylation Reaction" Glycobiology 17(9), 2007, 963-971.
McCart et al. "Developement of a Melanoma-Specific Adenovirus" Molecular Therapy, 6(4), 2002, 471-480.
Rojas et al. "Minimal RB-Responsive E1A Promoter Modification to Attain Potency, Selectivity, and Transgene-Arming Capacity in Oncolytic Adenoviruses" www.moleculartherapy.org, 18(11), 2010, 1960-1971.
Sherwood "Relaxin's Physiological Roles and Other Diverse Actions" Endocrine Reviews, 25(2), 2004, 205-234.
Smith et al. "Adenovirus Serotype 5 Fiber Shaft Influences In Vivo Gene Transfer in Mice" Human Gene Therapy, (2003), 14, 777-787.
Stern "Devising a Pathway for Hyaluronan Catabolismare we There Yet?" Glycobiology (2003), 13(12) 105R-115R.
Zhang et al. "Adenovirus Receptors" Journal of Virology (2005), 12125-12131.
Baumgartner et al. "The impact of extracellular matrix on the chemoresistance of solid tumors—experimental and clinical results of hyaluronidase as additive to cytostatic chemotherapy" (1998) Cancer Lett 131:85-99.
Rivera et al. "Mode of transgene expression after fusion to early or late viral genes of a conditionally replicating adenovirus via an optimized internal ribosome entry site in vitro and in vivo" (2004) Virology, 320(1):121-34.
Alemany et al. "Replicative adenoviruses for cancer therapy", Nature Biotechnology, vol. 18, (Jul. 2000) 723-727.
Baumgartner et al. "Hyaluronidase in der zytostatischen Therapie von HNO-Tumoren" Laryng. Rhino. Otol., 66(1987) 195-199. (Abstract).
Bazan-Peregrino et al. "Cavitation-enhanced delivery of a replicating oncolytic adenovirus to tumors using focused ultrasound" J. Controlled Release 169 (2013) 40-47.
Carlisle et al, "Enhanced Tumor Uptake and Penetration of Virotherapy Using Polymer Stealthing and Focused Ultrasound" J. Natl. Cancer Inst., (2013), 105:1701-1710.
El-Mogy et al. "Effect of adenovirus infection on transgene expression under the adenoviral MLP/TPL and the CMVie promoter/enhancer in CHO cells" Journal of Genetic Engineering and Biotechnology (2017) 15, 211-217.
Fang et al. "Kinetic Investigation of Recombinant Human Hyaluronidase PH20 on Hyaluronic Acid" ANalytical Biochemistry 480 (2015) 74-81.

(56) References Cited

OTHER PUBLICATIONS

Green et al. "Tropism ablation and stealthing of oncolytic adenovirus enhances systemic delivery to tumors and Improves virotherapy of cancer" Nanomedicine (2012) 7(11), 1683-1695.
Hofinger et al. "Isoenzyme-Specific Differences in the Degredation of Hyaluronic Acid by Mammalian-Type Hyaluronidases" Glycoconj J. (2008) 25:101-109.
Kelly et al. "History of Oncolytic Viruses: Genesis to Genetic Engineering" Molecular Therapy, vol. 15 No. 4, 651-659 (2007).
Kim et al. "Increased Cytopathic Effect of Replicating Adenovirus Expressing Adenovirus Death Protein" Cancer Research and Treatment (2003) 35(5), 425-432.
Klocker et al. "Hyaluronidase as additive to induction chemotherapy in advanced squamous cell carcinoma of the head and neck" Cancer Letters 131 (1998) 113-115.
Klonisch et al. "Relaxin-Like Ligand-Receptor Systems are Autocrine/Paracrine Effectors in Tumor Cells and Modulate Cancer Progression and Tissue Invasiveness" Relaxin and Related Peptides, (2007) Springer Science.
Leong et al. "High-Level Transcription from the Adenovirus Major Late Promoter Requires Downstream Binding Sites for Late-Phase-Specific Factors" Journal of Virology (1990) 51-60.
Lokeshwar et al. "Stromal and Epithelial Expression of Tumor Markers Hyaluronic Acid and HYAL 1 Hyaluronidase in Prostate Cancer" Journal of Biological Chemistry (2001) 276(15) 11922-11932.
Madan et al "Increased Hyaluronidase Expression in More Aggressive Prostate Adenocarcinoma" Oncology Reports (1999) 6:1431-1433.
Madan et al. "Association of Hyaluronidase and Breast Adenocarcinoma Invasiveness" Oncology Reports (1999) 6:607-609.
Maier et al. "Metaphylactic Effect of Mitomycin C with and without Hyaluronidase after Transurethral Resection of Bladder Cancer: Randomized Trial" Journal of Urology, (1988) 141:529-530.
Mo et al. "Increasing the density of nanomedicines improves their ultrasound-mediated delivery to tumours" Journal of Controlled Release 210 (2015) 10-18.
Smith et al. "Studies on the use of Viruses in the Treatment of Carcinoma of the Cervix" Cancer (1956) 9:1211-1218.
Smith et al. "Receptor Interactions Involved in Adenoviral-Mediated Gene Delivery After Systemic Administration in Non-Human Primates" Human Gene Therapy 14:1595-1604.
Stanton et al. "Re-engineering adenovirus vector systems to enable high-throughput analyses of gene function" BioTechniques 45:659-668.
Toth et al. "An Oncolytic Adenovirus Vector Combining Enhanced Cell-to-Cell Spreading, Mediated by the ADP Cytolytic Protein, with Selective Replication in Cancer Cells with Deregulated Wnt Signaling" Cancer Research 64, 3638-3644.
Ying et al. "INGN 007, an oncolytic adenovirus vector, replicates in Syrian hamsters but not mice: comparison of biodistribution studies" Cancer Gene Ther. (2009) 16(8): 625-637.
Hofinger et al. "Recombinant Human, Hyaluronidase Hyal-1: Insect Cell Versus *Escherichia coli* as Expression System and Identification of Low Molecular Weight Inhibitors" Glycobiology (2007), 17(4), 444-453.
Ganesh et al. "Relaxin-espressing fiber chimeric oncolytic adenovirus prolongs survival of tumor-bearing mice". Cancer Res (2007); 67:(9), pp. 4399-4407.
Ganesh et al. "Intratumoral coadministration of hyaluronidase inzyme and oncolytic adenoviruses inhances virus potency in metastatic tumor models" Clin. Cancer Res (2008); 14(12), pp. 3933-3941.
Yun "Overcoming the extracellular matrix barrier to improve intratumoral spread and therapeutic potential of oncolytic virotherapy" Current Opinion in Molecular Therapeutics (2008), vol. 10(4), pp. 356-361.
Kim et al "Relaxin expression from tumor-targeting adenoviruses and its intratumoral spread, apoptosis induction, and efficacy", Journal of the National Cancer Institute, vol. 98, No. 20, pp. 1482-1493.

Cheng et al "Human Matrix Metalloproteinase-8 Gene Delivery Increases the Oncolytic Activity of a Replicating Adenovirus", Molecular Therapy, vol. 15, No. 11, 2007, pp. 1982-1990.
Toole et al "Hyaluronan; A constitutive regulator of chemoresistance and malignancy in cancer cells", Semin. Cancer Biol. Aug. 2008; 18(4): 244-250.
Guedan et al "Hyaluronidase Expression by an Oncolytic Adenovirus Enhances Its Intratumoral Spread and Suppresses Tumor Growth", Molecular Therapy, vol. 18, No. 7, 1275-1283, May 2010.
Ko et al. "Development of transcriptionally regulated oncolytic adenoviruses", Oncogene (2005) 24, 7763-7774.
Reid et al. "Intravascular adenoviral agents in cancer patients: Lessons from clinical trials", Cancer Gene Therapy (2002) 9, 979-986.
Sauthoff et al. "Intratumoral Spread of Wild-Type Adenovirus is Limited After Local Injection of Human Xenograft Tumors: Virus Persists and Spreads Systemically at Late Time Points", Human Gene Therapy, 14:425-433, 2003.
Majem et al. "Control of E1A under an E2F-1 promoter insulated with the myotonic dystrophy locus insulator reduces the toxicity of oncolytic adenovirus Ad-D24RGD" Cancer Gene Therapy (2006) 13, 696-705.
Dmitriev et al. "An Adenovirus Vector with Genetically Modified Fibers Demonstrates Expanded Tropism via Utilization of a Coxsackievirus and Adenovirus Receptor-Independent Cell Entry Mechanism" Journal of Virology, vol. 72, No. 12, 1998, p. 9706-9713.
Suzuki et al. "A Conditionally Replicative Adenovirus with Enhanced Infectivity Shows Improved Oncolytic Potency" Clinical Cancer Research, vol. 7, pp. 120-126, 2001.
Carette et al. "Conditionally Replicating Adenoviruses Expressing Short Hairpin RNAs Silence the Expression of a Target Gene in Cancer Cells" Cancer Research, 64, 2663-2667, 2004.
Ikegami-Kawai et al. "Microanalysis of hyaluronan oligosaccharides by polyacrylamide gel electrophoresis and its application to assay of hyaluronidase activity" Analytical Biochemistry 311 (2002) 157-165.
Bayo-Puxan et al. "Replacement of Adenovirus Type 5 Fiber Shaft Heparan Sulfate Proteoglycan-Binding Domain with RGD for Improved Tumor Infectivity and Targeting" Human Gene Therapy 20:1214-1221, 2009.
Cascallo et al. "Systemic Toxicity-Efficacy Profile of ICOVIR-5, a Potent and Selective Oncolytic Adenovirus Based on the pRB Pathway" Molecular Therapy, vol. 15 No. 9, 1607-1615, 2007.
Gmachl et al. "The human sperm protein PH-20 has hyaluronidase activity" FEBS Letters, vol. 336, No. 3, pp. 545-548, 1993.
Czejka et al. "Influence of hyaluronidase on the blood plasma levels of 5-fluorouracil in patients" Pharmazie, 45:H9, 1990, pp. 693-694.
Bookbinder et al. "A recombinant human enzyme for enhanced interstitial transport of therapeutics" Journal of Controlled Release 114 (2006) 230-241.
Lin et al. "Molecular cloning of the human and monkey sperm surface protein PH-20", Proc. Natl. Acad. Sci. USA vol. 90, pp. 10071-10075, 1993.
Li et al. "Importance of Glycosylation and Disulfide Bonds in Hyaluronidase Activity of Macaque Sperm Surface PH-20" Journal of Andrology, vol. 23, No. 2, 2002, pp. 211-219.
Hunnicutt et al. "Structural Relationship of Sperm Soluble Hyaluronidase to the Sperm Membrane Protein PH-20" Biology of Reproduction 54, 1343-1349 (1996).
Van Ormondt et al. "The nucleotide sequence of the transforming early region E1 of adenovirus type 5 DNA" Gene, 11 (1980) 299-309.
Fueyo et al. "A mutant oncolytic adenovirus targeting the Rb pathway produces anti-glioma effect in vivo" Oncogene (2000) 19, 2-12.
Garcia-Castro et al. "Tumor cells as cellular vehicles to deliver gene therapies to metastatic tumors" Cancer Gene Therapy (2005) 12, 341-349.
Kaelin et al. "Expression Cloning of a cDNA Encoding a Retinoblastoma-Binding Protein with E2F-like Properties" Cell, vol. 70, 351-364, 1992.

(56) References Cited

OTHER PUBLICATIONS

Jin et al. "Identification of Novel Insertion Sites in the Ad5 Genome That Utilize the Ad Splicing Machinery for Therapeutic Gene Expression" Molecular Therapy, vol. 12, No. 6, 2005, pp. 1052-1063.
Kozak et al. "Point Mutations Define a Sequence Flanking the AUG Initiator Codon That Modulates Translation by Eukaryotic Ribosomes" Cell, vol. 44, 283-292, 1986.
Shan et al. "Molecular Cloning of Cellular Genes Encoding Retinoblastoma-Associated Proteins: Identification of a Gene with Properties of the Transcription Factor E2F" Molecular and Celllular Biology, 1992, vol. 12(12), pp. 5620-5631.
Helin et al. "A cDNA Encoding a pRB=Binding Protein with Properties of the Transcription Factor E2F" Cell, vol. 70, 337-350, 1992.
Pasqualini et al. "αv Integrins as receptors for tumor targeting by circulating ligands" Nature Biotechnology, vol. 15, 1997, pp. 542-546.
Dechecci et al. "Heparan Sulfate Glycosaminoglycans are Receptors Sufficient to Mediate the Initial Binding of Adenovirus Types 2 and 5" Journal of Virology, 2001, p. 8772-8780.
Athrop et al. "eDNA Cloning Reveals the Molecular Structure of a Sperm Surface Protein, PH-20, Involved in Sperm-Egg Adhesion and the Wide Distribution of its Gene among Mammals" The Journal of Cell Biology, vol. 111 (No. 6, Pt. 2), Dec. 1990 2939-2949.
Bayo-Puxan et al. "Role of the putative heparan sulfate glycosaminoglycan-binding site of the adenovirus type 5 iber shaft on liver detargeting and knob-mediated retargeting" 2006. Journal of General Virology, 87:2487-2495.
Ylá-Herttuala, Endgame: Glybera Finaly Recommended for Approval as the First Gene Therapy Drug in the European Union, Oct. 2012, Mol. Ther. 20; 10: 1831-2.
Wilson, "Gendicine: The First Commercial Gene Therapy Product," Sep. 2005 Human Gene Ther 16:1014. http://simodecshk.com/index.php/publications.
Raty et al., "Gene Therapy: The First Approved Gene-Based Medicines, Molecular Mechanisms and Clinical Indications", 2008 Molecular Pharmacology, 1:13-23.
Kim et al. A Phase I clinical trial of AD5/3-delta24, a novel serotype-chimeric, infectivity-enhance, conditionally-replicative adenovirus (CRAd) in patients with recurrent ovarian cancer, 2013, pp. 1-7.
Freytag "Phase I Study of Replication-Compentent Adenovirus-Mediated Double-Suicide Gene Therapy in Combination with conventional-Dose Three-Dimensional Conformal Radiation Therapy for the Treatment of Newly Diagnosed, Intermediate-High-Risk Prostate Cancer," Cancer Research, 2003; 63: 7497-7506.
Burke et al. "A First in Human Phase 1 Study of CG0070, a GM-CSF Expressing Oncolytic Adneovirus, for the Treatment of Nonmusle Invasive Bladder Cancer," J. Urology, 2012, 188(6):2391-2397.
Wirth et al. "History of gene Therapy", Gene, 2013, 525:162-169.
Darr et al. "Phylogeny and primary structure analysis of fiber shafts of all human adenovirus types for rational design of adenoviral gene-therapy vectors" Journal of General Virology (2009), 90, 2849-2854.
Jones et al. "Isolation of Adenovirus Type 5 Host Range Deletion Mutants Defective for Transformation of Rat Embryo Cells" Cell (1979) 17, 683-689.
Whatcott et al. "Targeting the Tumor Microenvironment in Cancer: Why Hyaluronidase Deserves a Second Look" Cancer Discov. (2011), 1(4), 291-296.
Reddy et al. "Enhanced Gene Transfer and Oncolysis of Head and Neck Cancer and Melanoma Cells by Fiber Chimeric Oncolytic Adenoviruses" (2006), 12(9), 2869-2878.
Kanerva et al. "Modified Adenoviruses for Cancer Gene Therapy", Int. J. Cancer (2004), 110, 475-480.
Stern et al. "Mammalian Hyaluronidases" (2000), Glycotorum, 1-6.
Guedan et al. "Syncytia Formation Affects the Yield and Cytotoxicity of an Adenovirus Expressing a Fusogenic Glycoprotein at a Late Stage of Replication" Gene Ther. (2008), 15(17), 1240-1245.
Fu et al. "A Strict-Late Viral Promoter is a Strong Tumor-Specific Promoter in the Context of an Oncolytic Herpes Simplex Virus" Gene Therapy (2003) 10, 1458-1464.
Lukashev et al. "Late Expression of Nitroreductase in an Oncolytic Adenovirus Sensitizes Colon Cancer Cells to the Prodrug CB1954" Human Gene Therapy (2005) 16:1473-1483.
Dipaolo et al. "Fiber Shaft-Chimeric Adenovirus Vectors Lacking the KKTK Motif Efficiently Infect Liver Cells In Vivo" Journal of Virology (2007), 12249-12259.

\* cited by examiner

IIIa                  K

TACTAAGCGGTGATGTTTCTGATCAGCCACCATGGGAGTGCTAAAATTCA
AGCACATCTTTTTCAGAAGCTTTGTTAAATCAAGTGGAGTATCCCAGATA
GTTTTCACCTTCCTTCTGATTCCATGTTGCTTGACTCTGAATTTCAGAGCA
CCTCCTGTTATTCCAAATGTGCCTTTCCTCTGGGCCTGGAATGCCCCAAG
TGAATTTTGTCTTGGAAAATTTGATGAGCCACTAGATATGAGCCTCTTCTC
TTTCATAGGAAGCCCCCGAATAAACGCCACCGGGCAAGGTGTTACAATAT
TTTATGTTGATAGACTTGGCTACTATCCTTACATAGATTCAATCACAGGAG
TAACTGTGAATGGAGGAATCCCCCAGAAGATTTCCTTACAAGACCATCTG
GACAAAGCTAAGAAAGACATTACATTTTATATGCCAGTAGACAATTTGGG
AATGGCTGTTATTGACTGGGAAGAATGGAGACCCACTTGGGCAAGAAAC
TGGAAACCTAAAGATGTTACAAGAATAGGTCTATTGAATTGGTTCAGCA
ACAAAATGTACAACTTAGTCTCACAGAGGCCACTGAGAAAGCAAAACAAG
AATTTGAAAAGGCAGGGAAGGATTTCCTGGTAGAGACTATAAAATTGGGA
AAATTACTTCGGCCAAATCACTTGTGGGGTTATTATCTTTTCCGGATTGT
TACAACCATCACTATAAGAAACCCGGTTACAATGGAAGTTGCTTCAATGT
AGAAATAAAAGAAATGATGATCTCAGCTGGTTGTGGAATGAAAGCACTG
CTCTTTACCCATCCATTTATTTGAACACTCAGCAGTCTCCTGTAGCTGCTA
CACTCTATGTGCGCAATCGAGTTCGGGAAGCCATCAGAGTTTCCAAAATA
CCTGATGCAAAAAGTCCACTTCCGGTTTTTGCATATACCCGCATAGTTTTT
ACTGATCAAGTTTTGAAATTCCTTTCTCAAGATGAACTTGTGTATACATTT
GGCGAAACTGTTGCTCTGGGTGCTTCTGGAATTGTAATATGGGGAACCC
TCAGTATAATGCGAAGTATGAAATCTTGCTTGCTCCTAGACAATTACATG
GAGACTATACTGAATCCTTACATAATCAACGTCACACTAGCAGCCAAAAT
GTGTAGCCAAGTGCTTTGCCAGGAGCAAGGAGTGTGTATAAGGAAAAAC
TGGAATTCAAGTGACTATCTTCACCTCAACCCAGATAATTTTGCTATTCAA
CTTGAGAAAGGTGGAAAGTTCACAGTACGTGGAAAACCGACACTTGAAG
ACCTGGAGCAATTTTCTGAAAAATTTTATTGCAGCTGTTATAGCACCTTGA
GTTGTAAGGAGAAAGCTGATGTAAAAGACACTGATGCTGTTGATGTGTGT
ATTGCTGATGGTGTCTGTATAGATGCTTTTCTAAAACCTCCCATGGAGAC
AGAAGAACCTCAAATTTTCTACAATGCTTCACCCTCCACACTATCTTAATA
AA [SEQ ID. NO. 4]

polA

MGVLKFKHIFFRSFVKSSGVSQIVFTFLLIPCCLTLNFRAPPVIPNVPFLWAW
NAPSEFCLGKFDEPLDMSLFSFIGSPRINATGQGVTIFYVDRLGYYPYIDSITG
VTVNGGIPQKISLQDHLDKAKKDITFYMPVDNLGMAVIDWEEWRPTWARNW
KPKDVYKNRSIELVQQQNVQLSLTEATEKAKQEFEKAGKDFLVETIKLGKLLR
PNHLWGYYLFPDCYNHHYKKPGYNGSCFNVEIKRNDDLSWLWNESTALYP
SIYLNTQQSPVAATLYVRNRVREAIRVSKIPDAKSPLPVFAYTRIVFTDQVLKF
LSQDELVYTFGETVALGASGIVIWGTLSIMRSMKSCLLLDNYMETILNPYIINV
TLAAKMCSQVLCQEQGVCIRKNWNSSDYLHLNPDNFAIQLEKGGKFTVRGK
PTLEDLEQFSEKFYCSCYSTLSCKEKADVKDTDAVDVCIADGVCIDAFLKPPM
ETEEPQIFYNASPSTL(SA)TMFIVSILFLIISSVASL  [SEQ ID. NO. 1]

B)

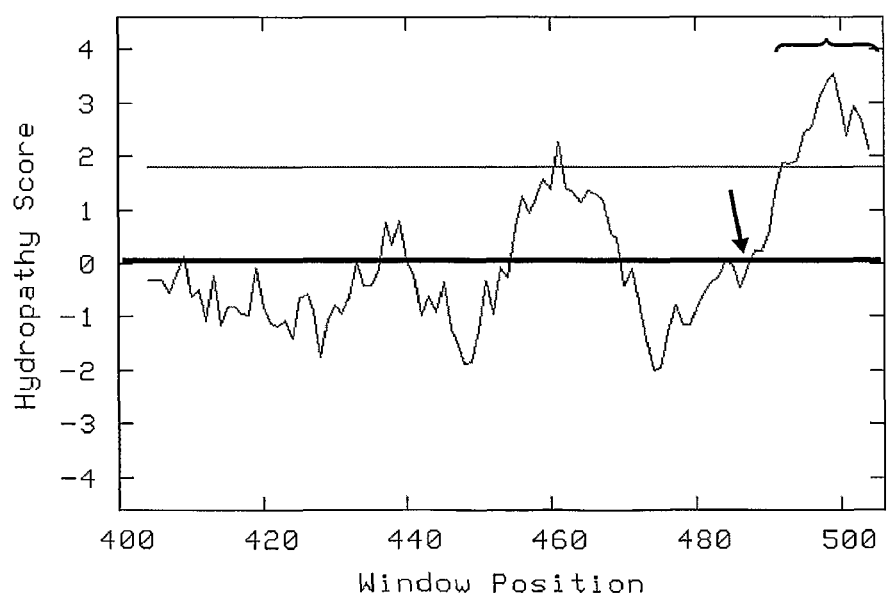

FIG. 4
A)
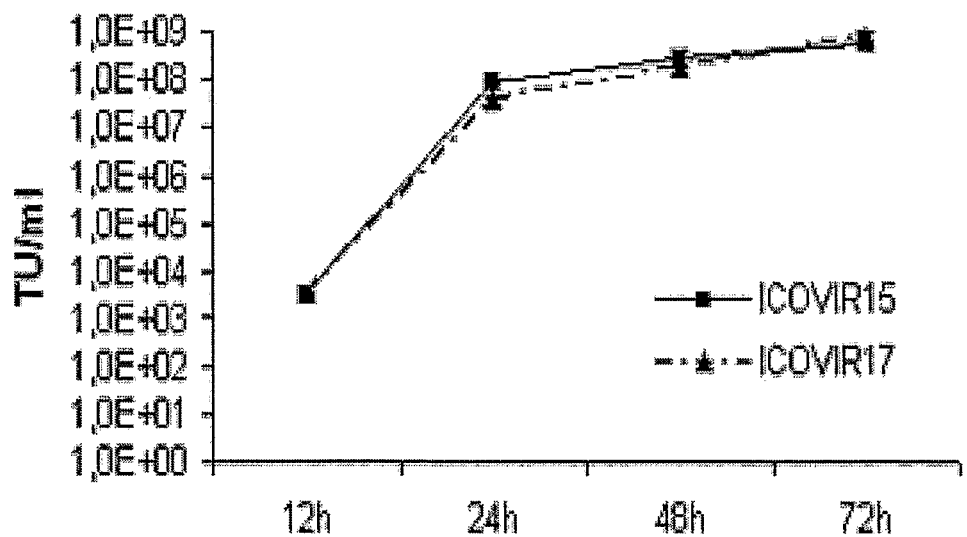
B)
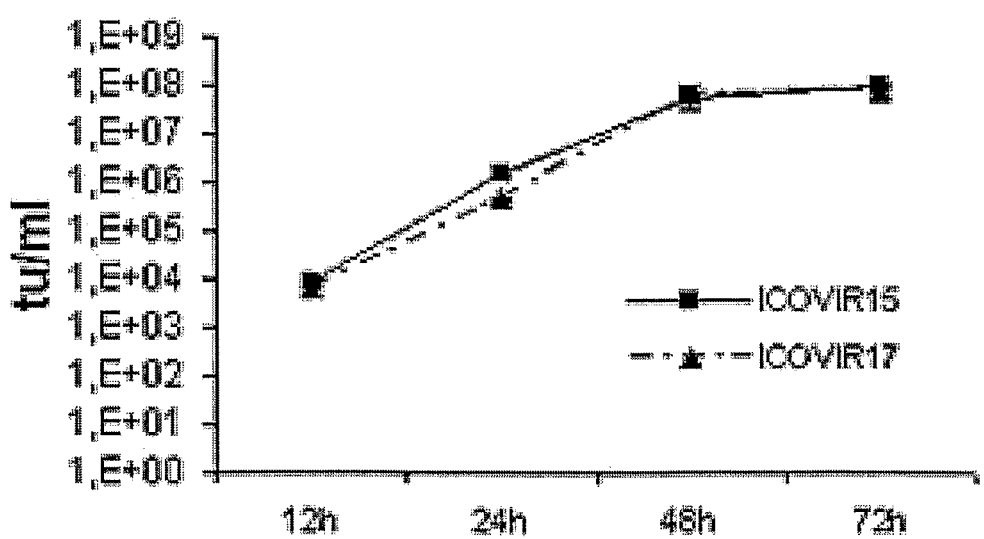

FIG. 5
A)
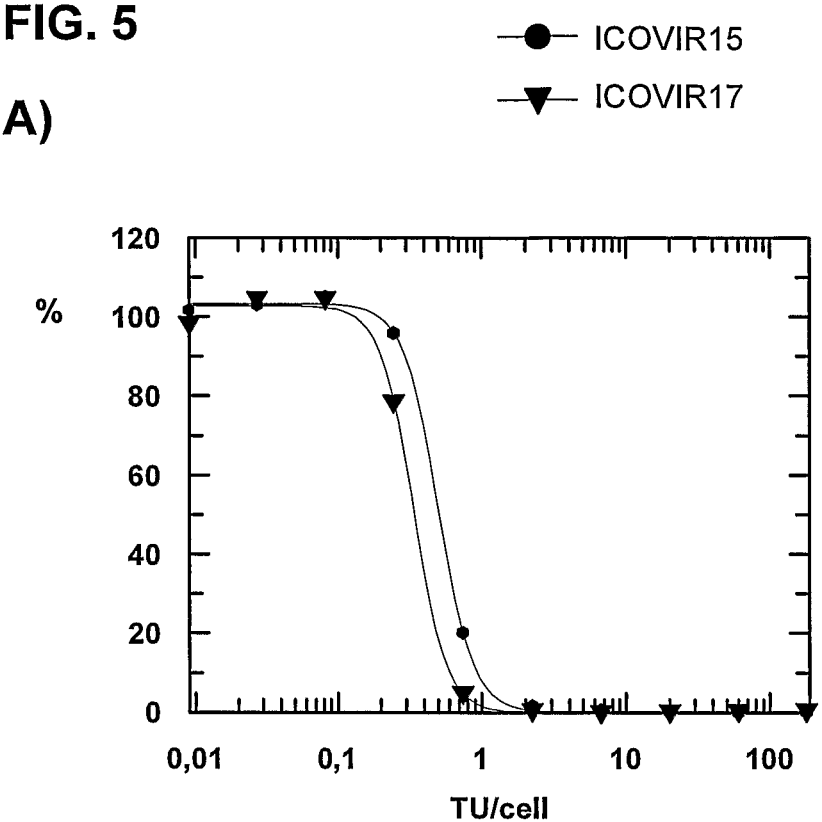
B)
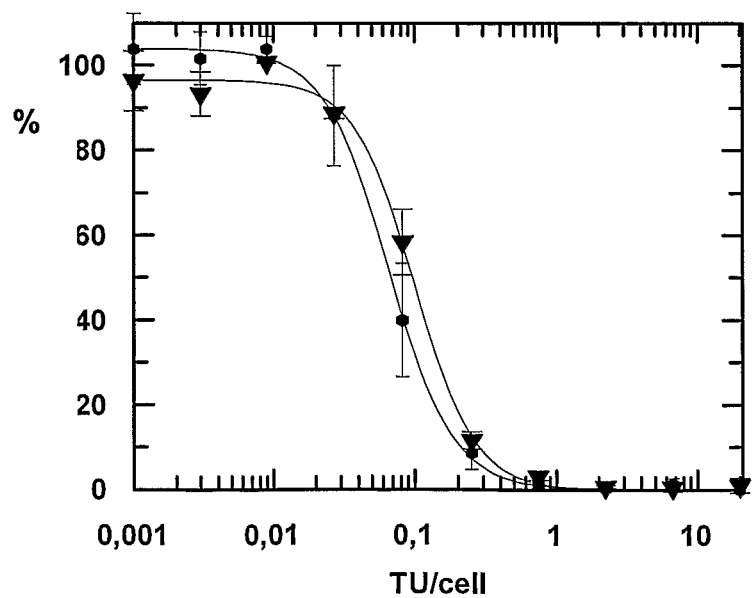

FIG. 6
A)
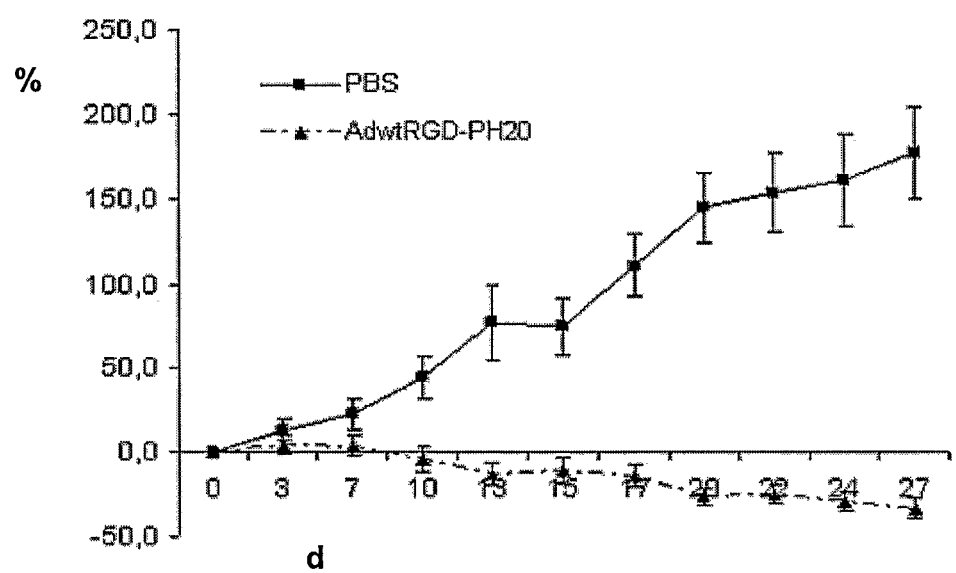
B)
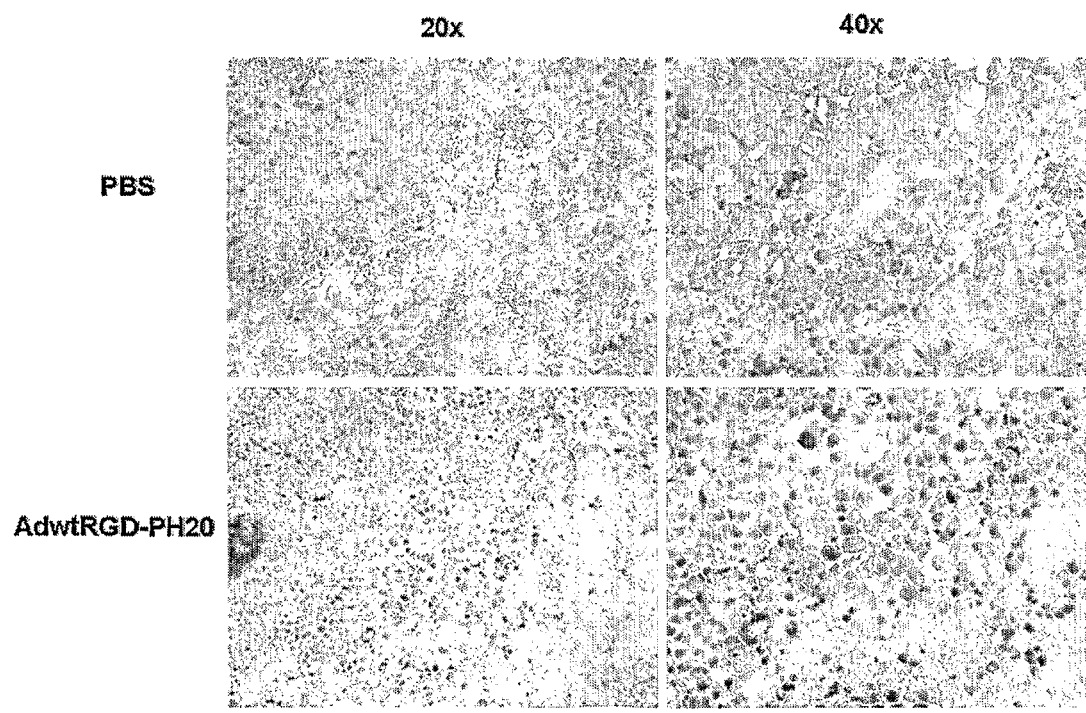

A)

B)

|  | Tumour volume day 0 | Tumour volume day 49 | % tumour growth day 49 | Tumour weight day 49 | % weigth vs PBS |
|---|---|---|---|---|---|
| PBS | 123.86 | 394.3 | 207.17 | 0.552 | 100 |
| ICOVIR15 | 129.2 | 221.6 # | 82.8 # | 0.342 | 61.95 |
| ICOVIR17 | 128.4 | 137.6 # | 12.2 # | 0.199 * # | 36.12 |

FIG. 8
A)
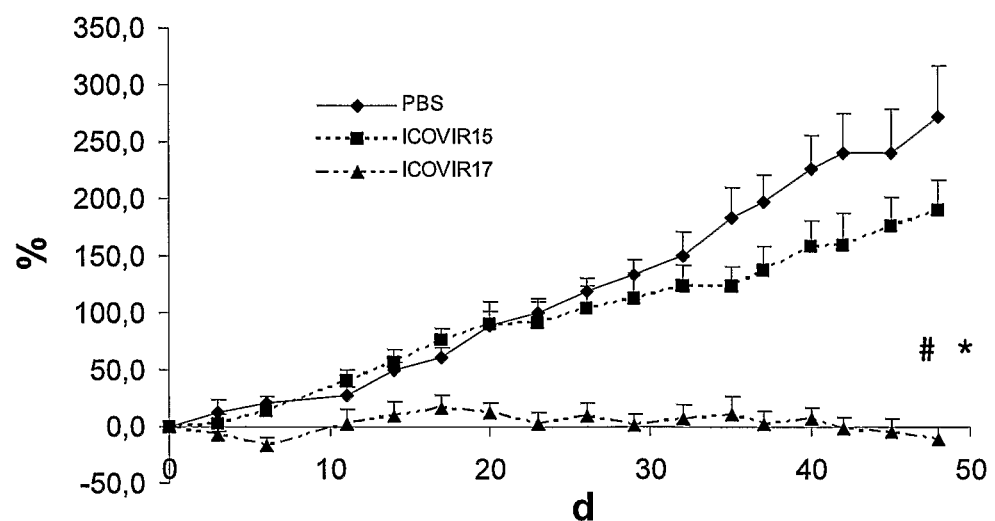
B)
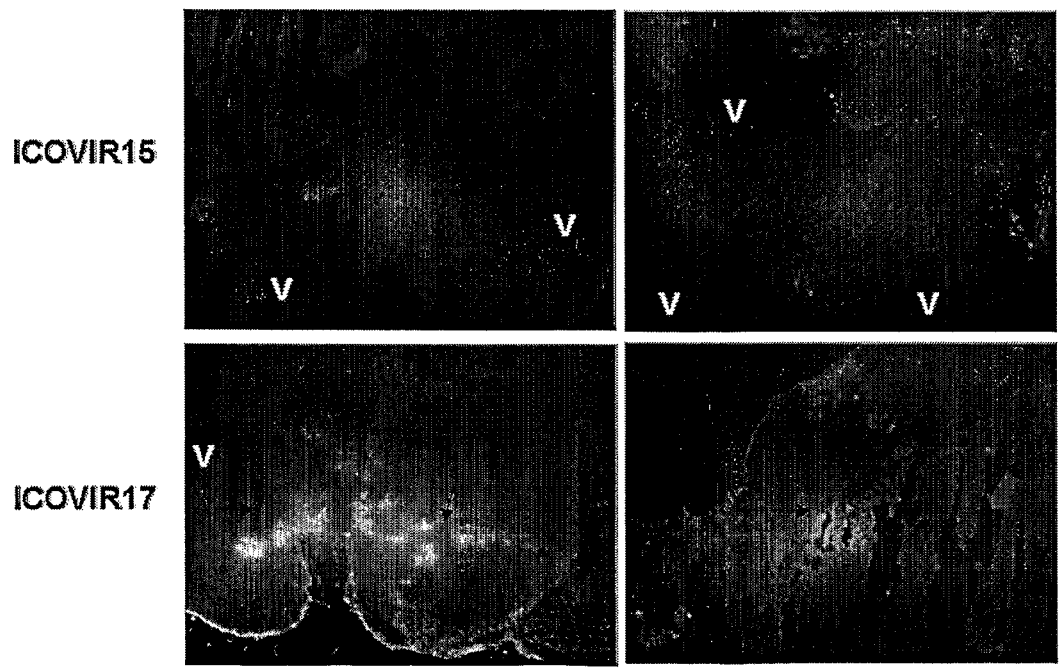

FIG. 9
A)
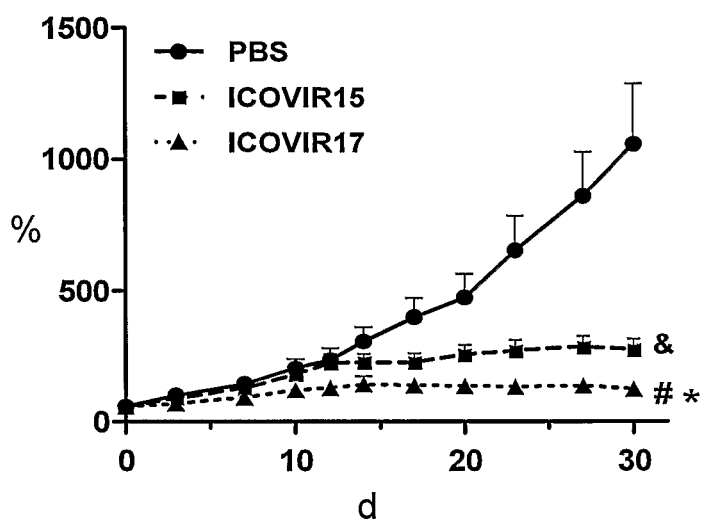
B)
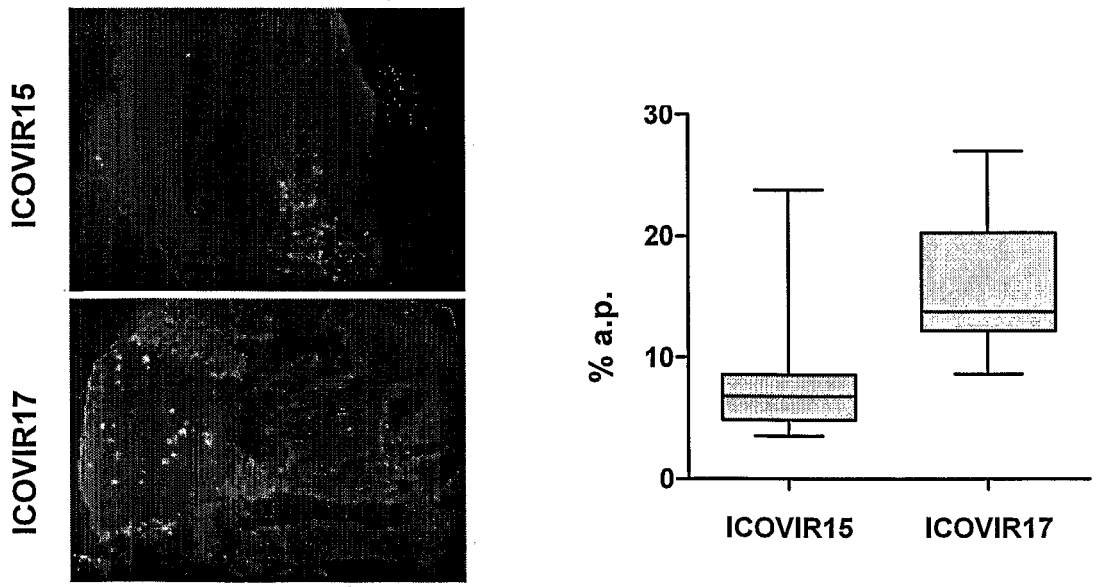

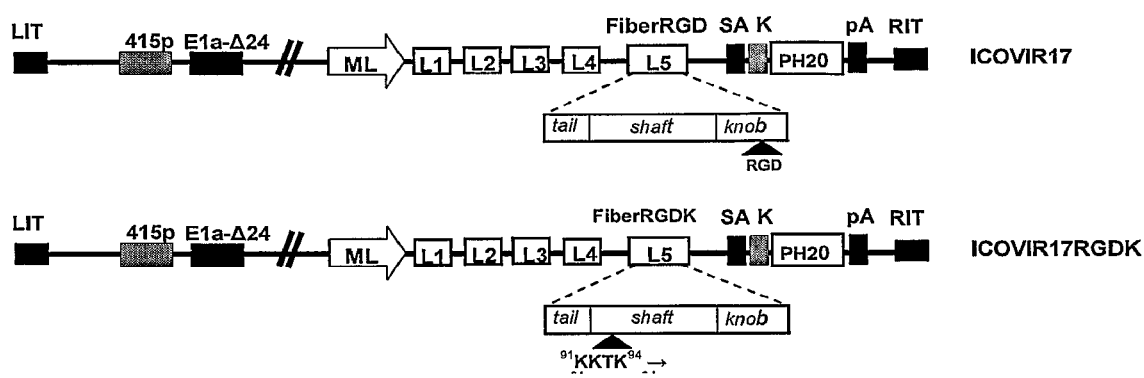

B)

¹MKRARPSEDTFNPVYPYDTETGPPTVPFLTPPFVSPNGFQES
PPGVLSLRLSEPLVTSNGMLALKMGNGLSLDEAGNLTSQNVT
TVSPPLRGDKSNINLEISAPLTVTSEALTVAAAAPLMVAGNTLT
MGSQAPLTVHDSKLSIATQGPLTVSEGKLALQTSGPLTTTDSS
TLTITASPPLTTATGSLGIDLKEPIYTQNGKLGLKYGAPLHVTDD
LNTLTVATGPGVTINNTSLGTKVTGALGFDSQGNMQLNVAGG
LRIDSQNRRLILDVSYPFDAQNQLNLRLGQGPLFINSAHNLDIN
YNKGLYLFTASNNSKKLEVNLSTAKGLMFDATAIAINAGDGLEF
GSPNAPNTNPLKTKIIGHGLEFDSNKAMVPKLGTGLSFDSTGAI
TVGNKNNDKLTLWTTPAPSPNCDLNAEKDAKLTLVLTKCGSQI
LATVSVLAVKGSLAPISGTVQSAHLIIRFDENGVLLNNSFLDPEY
WNFRNGDLTEGTAYTNAVGFMPNLSAYPKSHGKTAKSNIVSQ
VYLNGDKTKPVTLTITLNGTQETGDTTPSAYSMSFSWDWSGH
NYINEIFATSSYTFSYIAQE$^{582}$   [SEQ ID. NO. 9]

FIG. 11
A)
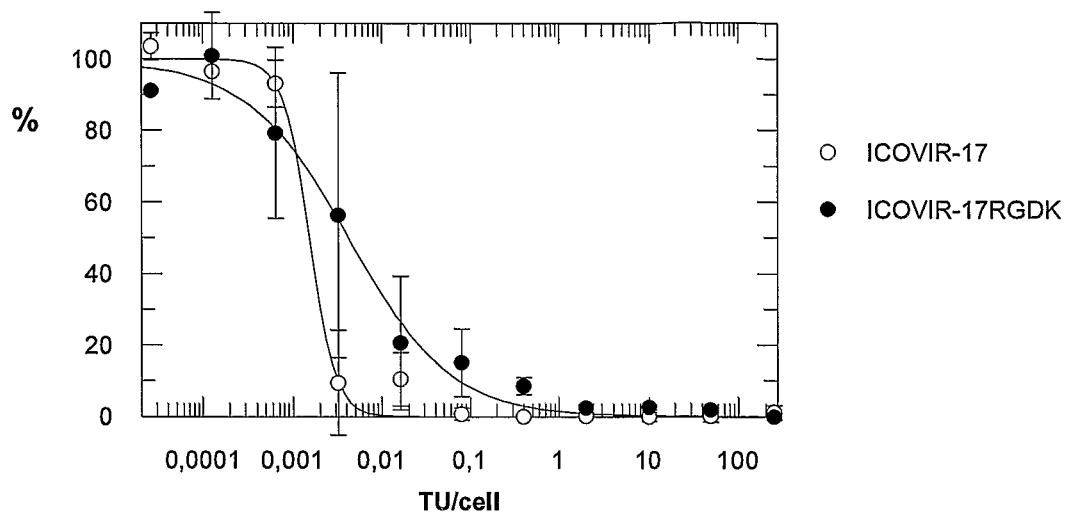
○ ICOVIR-17
● ICOVIR-17RGDK
B)
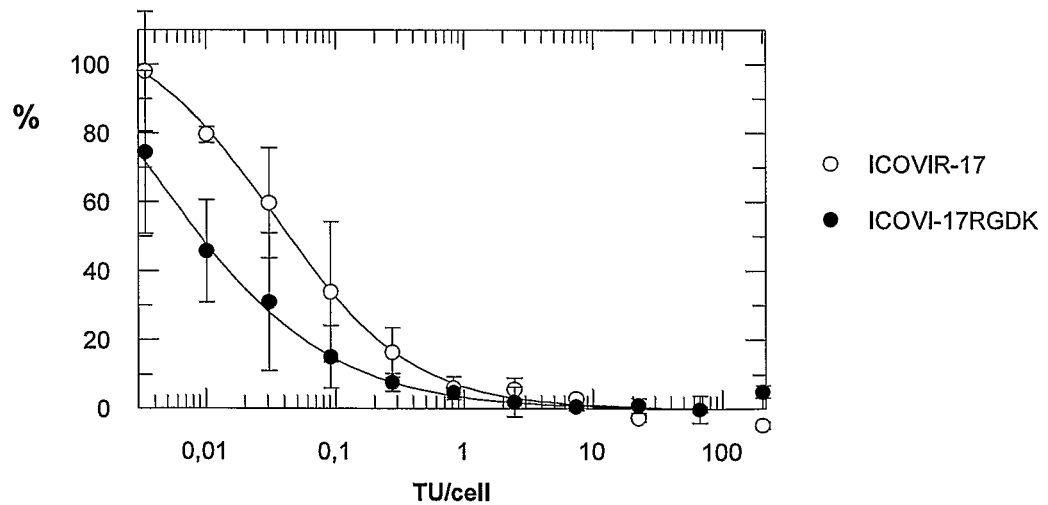
○ ICOVIR-17
● ICOVI-17RGDK

ONCOLYTIC ADENOVIRUSES FOR TREATING CANCER

The present application is a continuation of U.S. patent application Ser. No. 13/318,876, filed Mar. 5, 2012 which is a 371 of PCT Application PCT/ES2010/000196, filed May 5, 2010, which claims priority to Spanish Application Serial No. P200901201, filed May 6, 2009.

Oncolytic Adenoviruses for Treating Cancer

The invention is related to the field of the medicine, more particularly with the field of the oncology, and specifically with virotherapy.

BACKGROUND ART

Current cancer treatment is based mainly on chemotherapy, radiotherapy and surgery. In spite of an elevated rate of cure for cancer at early stages, most advanced cases of cancer are incurable because they cannot be extirpated surgically or because the doses of radio or chemotherapy administered are limited by their toxicity in normal cells. In order to palliate this situation, biotechnology strategies have been developed that seek to increase the potency and selectivity of oncology treatments. Among them, gene therapy and virotherapy use viruses with a therapeutic intention against cancer. In gene therapy the virus is modified to prevent its replication and to serve as vehicle or vector of therapeutic genetic material. On the contrary, virotherapy uses virus that replicate and propagate selectively in tumour cells. In virotherapy the tumour cell dies by the cytopathic effect caused by the replication of the virus in its interior rather than by the effect of a therapeutic gene. The preferential replication in a tumour cell is named oncotropism and the lysis of the tumour is named oncolysis. In a strict sense, viruses that replicate selectively in tumours are named oncolytic, although in a broader sense the oncolytic word can be applied to any replication-competent virus able to lyse tumour cells, even without selectivity. In this description the oncolytic term is used in both senses.

Virotherapy of the cancer is previous to gene therapy. The first observations of cures of tumours with viruses date from the beginning of the last century. In 1912 De Pace obtained tumour regressions after inoculating rabies virus in cervical carcinomas. Since then many types of viruses have been injected in tumours for their treatment. There are viruses that display a natural oncotropism such as autonomous parvovirus, vesicular stomatitis virus, and reovirus. Other viruses can be manipulated genetically to replicate selectively in tumours. For example, Herpes Simplex virus (HSV) has become oncotropic by eliminating the ribonucleotide reductase gene, an unnecessary enzymatic activity in cells in active proliferation such as tumour cells. However, adenovirus, due to its low pathogenicity and high capability to infect tumour cells has been the virus more often used in virotherapy and in gene therapy of cancer.

Fifty one human serotypes of adenovirus have been identified and classified in 6 different groups from A to F.

Adenovirus human type 5 (Ad5), that belongs to group C, is a virus formed by a protein icosahedral capsid that packages a linear DNA of 36 kilobases. In adults the infection with Ad5 is usually asymptomatic and in children it causes a common cold and conjunctivitis. In general Ad5 infects epithelial cells, which in the course of a natural infection are the cells of the bronchial epithelium. It enters the cell by means of the interaction of the fibre, the viral protein that extends as an antenna from the twelve vertices of the capsid, with a cellular protein involved in intercellular adhesion named Coxsackie-Adenovirus Receptor (CAR). When the viral DNA arrives at the interior of the nucleus, it begins an ordered transcription of the early genes (E1 to E4) of the virus. The first viral genes that are expressed are the genes of the early region 1A (E1A). E1A binds to the cellular protein Rb to release E2F, that activates the transcription of other viral genes such as E2, E3, and E4, and of cell genes that activate the cell cycle. On the other hand, E1B binds to p53 to activate the cell cycle and to prevent the apoptosis of the infected cell. E2 encodes proteins involved in virus replication; E3 encodes proteins that inhibit the antiviral immune response; E4 encodes for proteins involved in viral RNA transport. The expression of early genes leads to the replication of the virus DNA, and once the DNA has replicated, the major late promoter is activated and drives transcription of messenger RNA that upon differential splicing generates all the RNAs encoding for the structural proteins that form the capsid.

There are two important aspects to consider in relation to the design of oncolytic adenoviruses: selectivity and potency. In order to obtain selectivity towards the tumour cell three strategies have been used: the elimination of viral functions that are necessary for replication in normal cells but that are not needed in tumour cells; the control of the viral genes that start the replication using tumour-selective promoters; and the modification of the virus capsid proteins implied in the infection of the host cell. With these genetic modifications a considerable level of selectivity has been obtained, with a replication efficacy in tumour cells in the order of 10000 times superior to the replication efficacy in normal cells. With regard to oncolytic potency, several genetic modifications have also been described to increase it. These modifications include: a) the increase of virus release, for example by eliminating E1B19K, over-expressing E3-11.6K (ADP), or localizing E3/19K protein in the plasmatic membrane; and b) the insertion of a therapeutic gene in the genome of the oncolytic adenovirus to generate an "armed oncolytic adenovirus". In this case, the therapeutic gene would have to mediate the death of non-infected tumour cells by means of the activation of a prodrug with bystander effect (that is to say, that kills the non-infected neighbouring cells), the activation of the immune system against the tumour, the induction of the apoptosis, the inhibition of the angiogenesis, or the elimination of the extracellular matrix, among others. In these cases, the way and the time of expression of the therapeutic gene will be critical in the final result of the therapeutic approach.

In the last decade, different oncolytic adenoviruses have been administered to patients with head and neck, ovarian, colorectal, pancreatic, and hepatocellular carcinomas, among others. The safety profile of these adenoviruses in clinical trials has been very promising. The detected adverse effects, such as flu-like symptoms and increase levels of transaminases, were well tolerated, even after the systemic administration of high doses of virus (cfr. D. Ko et al., "Development of transcriptionally regulated oncolytic adenoviruses", *Oncogene* 2005, vol. 24, pp. 7763-74; and T. Reid et al., "adenoviral Intravascular agents in cancer patients: lessons from clinical trials", *Cancer Gene Therapy* 2002, vol. 9, pp. 979-86). Although the administration of the recombinant adenovirus induced a partial suppression of tumour growth, the complete eradication of the tumours was not achieved and after a short period of time the tumours re-grew quickly. These results probably occurred because the injected adenovirus distributed only in a small part of the tumour to produce a limited antitumour response, as non-infected cells continued growing quickly. In a recent work, it was observed that the replication of oncolytic adenoviruses in human xenograft tumours persisted until 100 days after systemic administration, although this replication did not translate in a complete eradication of the tumour (cfr. H. Sauthoff et al., "Intratumoural spread of wild-type adenovirus is limited to after local injection of human xenograft tumours: virus persists and spreads systemically at late time points", *Human Gene Therapy* 2003, vol. 14, pp. 425-33). This low antitumour efficacy is in part because the connective tissue and the extracellular matrix (ECM) in the tumour prevent the spread of adenovirus within the tumour.

This difficulty of oncolytic adenoviruses to spread efficiently within the tumour mass has been described also for other antitumour drugs such as doxorubicin, taxol, vincristine, or methotrexate. Many studies demonstrate the role of the ECM in the resistance of tumour cells to chemotherapy drugs (cfr. B P Toole et al., "Hyaluronan: a constitutive regulator of chemoresistance and malignancy in cancer cells", *Seminars in Cancer Biology* 2008, vol. 18, pp. 244-50). Tumour and stromal cells produce and assemble a matrix of collagen, proteoglycans and other molecules that difficults the transport of macromolecules inside the tumour. Hyaluronic acid (HA) is one of the main components of the ECM involved in the resistance of tumour cells to therapeutic drugs. HA is overexpressed in a great variety of malignant tissues, and in many cases the level of HA is a factor tumour progression prognosis. The interaction of HA with receptors CD44 and RHAMM increases tumour survival and invasion. In addition, HA can promote tumour metastases by inducing cell adhesion and migration, and protection against the immune system.

On the other hand, the inhibition of the interactions between hyaluronic acid and tumour cells revert the resistance to many drugs. Different studies have indicated that hyaluronidases (enzymes that degrade HA) increase the activity of different chemotherapies in patients with melanoma, Kaposi sarcoma, head and neck tumours, and liver metastases of colon carcinoma. The mechanism of action of hyaluronidases is still unknown, but generally it is attributed to reducing cell adhesion barriers, reducing interstitial pressure, and improving penetration of the antitumour drug in the tumour, rather than to its inhibitory effects of signalling pathways related to cellular survival.

Recently, it has been described that the coadministration of hyaluronidase with oncolytic adenoviruses by means of intratumoural injection, reduces tumour progression (cfr. S. Ganesh et al., "Intratumoural coadministration of hyaluronidase enzyme and oncolytic adenoviruses enhances virus potency in mestastasic tumour models", *Clin Cancer Res* 2008, vol. 14, pp. 3933-41). In these studies oncolytic adenoviruses are administered in four intratumoural injections and hyaluronidase is administered intratumourally every other day during all the treatment. This regimen of administration has little application to patients because most of the tumours are inaccessible to be injected intratumourally. The patients with scattered disease (metastasis) could not benefit from the treatment proposed by Ganesh and collaborators.

In spite of the efforts to date, it is still necessary to find new therapeutic approaches effective in the treatment of the cancer.

SUMMARY OF THE INVENTION

The inventors have found that an adenovirus that replicates and contains the hyaluronidase gene in its genome is distributed more efficiently in the tumour mass. The expression of hyaluronidase by the oncolytic adenovirus results in the degradation of the hyaluronic acid which is part of the extracellular matrix of the tumour. The degradation of hyaluronic acid results in a lower interstitial pressure in the tumour and in a smaller resistance of the tumour to the spread of the adenovirus, and therefore, the cell to cell spread of the virus within the tumour mass improves. This better spread is translated in an increase of the oncolytic effect. The inventors have found that injecting the oncolytic adenovirus of the invention endovenously, regressions of the tumour volume are obtained. Therefore, the oncolytic adenovirus of the present invention is useful for the treatment of the cancer. In addition, the expression of the hyaluronidase gene does neither affect the viral replication nor the cytotoxicity of oncolytic adenovirus.

As mentioned before, it has been described that the intratumoural coadministration of an oncolytic adenovirus and soluble hyaluronidase increases the antitumour efficay of the oncolytic adenovirus. However, previous to this invention the hyaluronidase gene has not been introduced in any oncolytic adenovirus for the treatment of the cancer.

As it is described in the examples, the intratumoural in vivo administration of the oncolytic adenovirus of the invention improves the antitumour effect with respect to an adenovirus control without the inserted hyaluronidase (see FIG. 7). Of note, when the oncolytic adenovirus of the invention is injected endovenously (see FIG. 8 and FIG. 9) and, in comparison to the results presented in FIG. 2 of the manuscript of Ganesh et al., a much greater tumour growth inhibition is observed with the present invention adenovirus. This indicates that the treatment of the invention is more effective. The tumours of the mice injected with the oncolytic adenovirus of the invention (ICOVIR17) show very extensive necrotic areas, areas with less viable cells, and large and numerous centers of virus replication, in comparison with the tumours injected with the adenovirus control, ICOVIR15.

In addition, with the adenovirus of the invention the administered doses are smaller: in Ganesh et al. (supra) four intratumour injections of $1 \times 10^{19}$ viral particles are administered, whereas in the present invention a single endovenous dose of $2 \times 10^9$ viral particles is administered. This means a dose reduction of 20 times and the advantage of being a unique dose. In their approach, Ganesh et al. administer hyaluronidase intratumorally every other day throughout the experiment. In addition adenovirus also is administered intratumourally at the beginning of the treatment. This intratumour administration of virus and hyaluronidase it is hardly applicable to the clinic because most tumours are not accessible for an intratumoural administration. Presumably the soluble coadministration of hyaluronidase and adenovirus was not made by systemic route because the probability that both components reach together the scattered tumour cells in the organism is low.

The present invention allows the expression of hyaluronidase at the site and moment that viral replication takes place. This expression of hyaluronidase improves the distribution of the virus through the tumour mass and increases its antitumour potency. It is feasible to administer adjusted doses, non-toxic for the animal, with great efficacy for the treatment.

In the present invention, the oncolytic adenoviruses arrive at the target tumour cells. Once inside, the virus replicate, their capsid proteins are expressed and, at the same time, the hyaluronidase encoded in the adenoviral genome is expressed. This hyaluronidase has been modified to be released to the extracellular medium that surrounds the cells. In the extracellular medium, the hyaluronidase destroys the matrix and helps the adenoviruses that have replicated in infecting the neighbouring tumour cells.

Thus, an aspect of the invention refers to an oncolytic adenovirus which comprises a sequence encoding a hyaluronidase enzyme inserted in its genome.

As it is used herein, the term "oncolytic adenovirus" means an adenovirus that is able to replicate or that it is replication-competent in the tumour cell. In this description, oncolytic adenovirus and replicating adenovirus are synonymous. They are different from a non-replicating adenovirus because this latter is unable to replicate in the target cell. Non-replicating adenoviruses are the ones used in gene therapy as carriers of genes to target cells since the goal is to express the therapeutic gene within the intact cell and not the lysis of the cell. Instead, the therapeutic action of oncolytic adenoviruses is based on the capability to replicate and to lyse the target cell, and in particular the tumour cell to be eliminated.

Another aspect of the invention refers to a pharmaceutical composition which comprises a therapeutically effective amount of the oncolytic adenovirus, together with pharmaceutically acceptable carriers or excipients.

Another aspect of the invention refers to the oncolytic adenovirus of the invention for its use as a medicament.

Another aspect of the invention refers to the oncolytic adenovirus of the invention for the treatment of a cancer or a pre-malignant form of cancer in a mammal, including a human.

Another aspect of the invention refers to the use of the oncolytic adenovirus for the manufacture of a medicament for the treatment of a cancer or a pre-malignant form of cancer in a mammal, including a human. The treatment is based on the replication of these oncolytic adenoviruses in tumours. Alternatively, this aspect of the invention can be formulated as a method for the treatment in a mammal, including the man, of a cancer or a pre-malignant form of cancer, that comprises the administration to said mammalian of an effective amount of the oncolytic adenovirus.

Another aspect of the invention refers to a shuttle vector that is able to recombine with an adenoviral genome for the construction of the oncolytic adenovirus of the invention. This vector comprises inverted terminally repeated sequences of adenovirus ("inverted terminal repeats", ITRs), a sequence that promotes the expression of the sequence encoding the enzyme hyaluronidase, the sequence that encodes the enzyme, and a polyadenylation sequence.

In a particular embodiment, the oncolytic adenovirus of the invention is a human adenovirus, meaning that infects humans. Particularly, the human adenovirus is selected from the group consisting of human adenovirus serotypes 1-51 and derivatives thereof. It is meant as "derivative" a recombinant adenovirus hybrid of two or more different serotypes from adenovirus, e.g. serotype 5 adenovirus with the fibre of serotype 3 adenovirus. In a particular embodiment of the invention, the human oncolytic adenovirus is from serotype 5.

Hyaluronidases are an enzyme family that degrades hyaluronic acid. In humans there are 6 genes encoding for hyaluronidases with different properties and locations. Isoforms Hyal1 and Hyal2 are present in most tissues. Hyal1 is the predominant form in human plasma. Hyal3 is present in bone marrow and testis, but its function is not well characterized. Hyaluronidase PH20 is expressed highly in testis and is involved in the process of fertilization of the oocyte by the spermatozoon. Hyaluronidase PH20 is anchored to the plasmatic membrane and to the internal acrosomal membrane of the spermatozoa and confers to the spermatozoon the capability to penetrate through the extracellular matrix of the cumulus (rich in hyaluronic acid) to reach the pellucid zone of the oocyte. During the acrosomal reaction, part of the hyaluronidases anchored at the membrane of the spermatozoon is processed enzymatically to produce a soluble form of the protein that is released from the acrosomal membrane. In addition, hyaluronidase has been identified as the spreading factor of the poison of snakes, spiders, scorpions, and wasps.

In a particular embodiment, the enzyme hyaluronidase is a mammal testicular hyaluronidase, and more particularly, human testicular hyaluronidase. Human testicular hyaluronidase (GenBank GeneID: 6677) is also known as SPAM1 or sperm adhesion molecule 1, and as PH-20. The membrane protein PH20 is the only enzyme of the family of mammal hyaluronidases with activity at neutral pH. The gene that encodes it produces two transcriptional variants: variant 1, longer, than encodes the isoform 1 of the protein (GenBank access number NP 003108.2) and variant 2, that uses an alternative splicing signal at the 3' codifying region compared to variant 1, resulting in isoform 2 with a shorter C-terminus (GenBank access number NP_694859.1).

In a particular embodiment of the invention, the enzyme sequence is deleted at the sequence corresponding to the carboxy terminal membrane-binding domain to produce a soluble enzyme (see FIG. 2). The deletion of this carboxy terminal domain results in the secretion of the hyaluronidase to the extracellular medium. Thus, it has been obtained an oncolytic adenovirus that expresses a secreted hyaluronidase with enzymatic activity at neutral pH. In a particular embodiment, the sequence inserted in the adenoviral genome is one which encodes the SEQ ID NO: 1. In a more particular embodiment, the sequence inserted is the SEQ ID NO: 2.

In another embodiment, the sequence of the enzyme is inserted in the oncolytic adenovirus after the nucleotide sequence of the adenoviral fibre.

In another particular embodiment, the expression of the enzyme is controlled by a promoter active in animal cells. Particularly, the promoter is selected from the group consisting of the cytomegalovirus promoter, the adenovirus major late promoter, the SV40 promoter, the herpes simplex virus thymidine kinase promoter, the RSV promoter, the EF1 alpha promoter, the beta-actin promoter, the human IL-2 promoter, the human IL-4 promoter, the IFN promoter, the E2F promoter, and the human GM-CSF promoter. The promoter that controls the expression of the enzyme can be natural of the adenovirus as it is the case of the adenovirus major late promoter (see FIG. 1(a), MLP, "major late promoter"). The promoter can also be inserted next to the sequence that encodes for the enzyme. In a preferred embodiment, the promoter is the adenovirus major late promoter.

The replicative adenovirus of the invention can have modifications in its genomic sequence that confer selective replication in tumour cells. In a particular embodiment this is achieved with the insertion of a tissue-specific promoter or a tumour-specific promoter. This promoter controls the expression of one or more genes of the group of E1a, E1b, E2, and E4. Particularly, the promoter is selected from the group consisting of the E2F promoter, the telomerase hTERT promoter, the tyrosinase promoter, the prostate-specific antigen (PSA) promoter, the alpha-fetoprotein promoter, the COX-2 promoter, as well as artificial promoters formed by several transcription factor binding sites such as binding sites for the hypoxia induced factor (HIF-1), the Ets transcription factor, the tumour cytotoxic factor (tcf), the E2F transcription factor or the Sp1 transcription factor. Preferably the promoter controls the expression of E1a.

Another modification to obtain selective replication in tumours is the elimination of E1A functions that block the retinoblastoma (RB) pathway. Other viral genes that interact directly with pRB such as E4 and E4orf6/7 are candidates to be eliminated to obtain selective replication in tumour cells. As shown in the examples, the oncolytic adenovirus ICOVIR17 is characterized by containing simultaneously the gene of hyaluronidase, the Δ24 deletion that affects to the interaction of E1a with pRB, the insertion of four E2F1 binding sites and one Sp1 binding site in the endogenous promoter of E1a to control the expression of E1a, and finally, the insertion of the RGD peptide in the adenoviral fibre to increase the infectivity of the virus. ICOVIR17 is a preferred embodiment of the invention.

Another described modification to obtain selective replication in tumours is the elimination of the adenoviral genes that encode the virus-associated RNAs (VA-RNAs). These RNAs block the antiviral activity of the interferon and, when deleted, adenovirus becomes sensitive to be inhibited by interferon. Since tumour cells are characterized by the truncation of the interferon pathway, such adenoviruses replicate at normal levels in tumours. Thus, in another particular embodiment, the selective replication in tumours is obtained with mutations in one or more genes of the group of E1a, E1b, E4, and VA-RNAs of adenovirus. Preferably the mutations are in E1a.

These two strategies to obtain selective replication in tumours are not excluding each other.

In another embodiment of the invention, the adenovirus has modifications in its capsid to increase its infectivity or to direct it to a receptor present in a tumour cell. In a preferred embodiment the adenovirus capsid proteins have been modified genetically to include ligands that increase the infectivity or that direct the virus to a receptor in the tumour cell. Targeting adenovirus to the tumour can also be achieved with bifunctional ligands that bind to the virus on one side and to the tumour receptor the other. On the other hand, to increase the persistence of adenovirus in blood and therefore to increase the possibilities of reaching scattered tumour nodules, the capsid can be covered with polymers like polyethylene-glycol. In a preferred embodiment, the oncolytic adenovirus has the capsid modified to increase its infectivity or to direct it better to the target cell by means of a replacement of the KKTK heparan sulfate binding domain in the adenovirus fibre with the domain RGDK. In the examples the construction of an adenovirus with these characteristics, ICOVIR17RGDK, is explained.

In another particular embodiment, the adenovirus comprises a sequence that optimizes the translation into protein of the sequence that encodes the hyaluronidase.

In another particular embodiment, the adenovirus comprises a sequence that promotes the expression of the sequence that encodes the hyaluronidase. More particularly, this sequence is selected from the group consisting of a splicing sequence that allows the processing of the RNA, an IRES sequence ("internal ribosome entry site"), and the sequence 2A of picornavirus.

In another particular embodiment, the oncolytic adenovirus comprises other genes inserted in its genome that are used commonly in the field of cancer gene therapy to increase the cytotoxicity of oncolytic adenoviruses towards tumour cells. Some of them are the thymidine kinase gene, the cytosine deaminase gene, proapoptotic genes, immune-stimulatory genes, tumour suppressor or pro-drug activating genes.

These modifications in the genome of the adenovirus are not excluding each other. There are several methods to manipulate the adenoviral genome. The methods to construct genetically-modified adenovirus are well established in the field of the gene therapy and virotherapy with adenoviruses. The method more commonly used is based on constructing first the desired genetic modification in a plasmid that contains the adenoviral region to modify, and later performing an homologous recombination in bacteria with a plasmid that contains the rest of the viral genome.

The adenovirus that contains the hyaluronidase gene object of the present invention is propagated and amplified in cell lines normally used in the field of the gene therapy and virotherapy such as HEK-293 and A549 cell lines. The preferred method of propagation is by infection of a cell line permissive to the replication of adenovirus. The pulmonary adenocarcinoma cell line A549 is an example of a line with such characteristics. The propagation is performed for example in the following way: A549 cells are seeded on plastic cell culture plates and infected using 100 viral particles by cell. Two days later the cytopathic effect that reflects the virus production is observed as a clustering and rounding of the cells. The cells are harvested in tubes. After centrifugation at 1000 g during 5 minutes, the cell pellet is frozen and thawed three times to break the cells. The resulting cell extract is centrifuged at 1000 g during 5 minutes and the supernatant with virus is loaded on a cesium chloride gradient and centrifuged during 1 hour at 35000 g. The band of virus obtained from the gradient is loaded on another cesium chloride gradient and centrifuged again during 16 hours at 35000 g. The virus band is harvested and dialyzed against PBS-10% glycerol. The dialyzed virus is aliquoted and kept at −80° C. The quantification of the number of viral particles and plaque-forming units is done following standard protocols. The phosphate buffered saline (PBS) with glycerol to 5% is a standard formulation for the storage of adenovirus. Nevertheless new formulations have been described that improve the stability of the virus. The purification methods of the adenovirus that contains the hyaluronidase gene for its use in the treatment of the cancer are the same as those described for other adenoviruses and adenoviral vectors used in virotherapy and gene therapy of the cancer.

The oncolytic adenovirus of the present invention can be administered to a mammal, preferably a human. The intention of the administration of the oncolytic adenovirus is therapeutic, including, but not limiting, to melanoma, pancreas cancer, colon cancer and lung cancer. Also, it is considered the administration of the oncolytic adenovirus in a pre-malignant stage of a tumour.

It is understood that the oncolytic adenovirus is administered in a pharmaceutically acceptable form. The experts in the art can ensure the appropriate dose using standard procedures. It is understood that the dose must be an effective amount of oncolytic adenovirus to produce a reduction of the tumour in the treated patient. The virus can be administered directly in the tumour, in the cavity where the tumour is located, in the vasculature of the tumour, around the tumour, or by systemic endovenous injection in the patient. Preferably, the administration is systemic.

The protocols to use the viruses described in the present invention for the treatment of cancer are the same procedures used in the fields of virotherapy with adenovirus and gene therapy with adenovirus. There is a large experience in the use of non-oncolytic and oncolytic adenoviruses in the field of the gene therapy. There are numerous publications describing the treatment of tumour cells in culture, in animal models, and clinical trials with patients. For the treatment of cells in culture in vitro, the adenovirus purified by any of the formulations described above is added to the culture medium to obtain the infection of the tumour cells. In order to treat tumours in animal models or in patients adenovirus can be administered loco-regionally by injection in the tumour or in the body cavity where the tumour is located, or systemically by injection in the bloodstream.

The oncolytic adenovirus of the invention can be administered alone or in a composition with pharmaceutically acceptable carriers or excipients. The skilled in the art will adapt the composition according to the particular way of administration. The compositions can comprise the oncolytic adenovirus as the only agent against the tumour, or in combination with another therapeutic agent such as a chemotherapy drug or a vector with an inserted therapeutic gene. Also the oncolytic adenovirus therapy can be combined with radiotherapy.

Unless otherwise defined, all technical and scientific terms used herein have the same meaning as commonly understood by a personone of ordinary skilled in the art. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following particular embodiments and drawings are provided by way of illustration, and they are not intended to be limiting of the present invention.

DESCRIPTION OF THE DRAWINGS

FIG. 1(a) shows the structure of oncolytic adenoviruses characterized by containing and expressing the hyaluronidase gene PH20. Adenovirus AdwtRGD-PH20 contains the gene of protein PH20 inserted after the adenovirus fibre gene. The expression of the protein PH20 gene is regulated by the major late promoter (MLP) of the adenovirus by means of the insertion of the splicing acceptor IIIa of adenovirus (SA) before the protein PH20 gene. Protein translation of this gene is optimized due to the introduction of the kozak sequence (k) before the translation start sequence. Adenovirus ICOVIR15 and ICOVIR17 are tumour-selective replicating adenoviruses. They are characterized by containing 4 E2F binding sites and one Sp1 binding site in the endogenous promoter of E1a. Both viruses also present a modified version of the viral fibre where the peptide RGD-4C has been inserted, and a mutant version of E1A protein where amino acids 121-129 of the polypeptide chain have been deleted (Δ24 mutation). In addition, ICOVIR17, contains the hyaluronidase PH20 gene inserted as in AdwtRGD-PH20 adenovirus. (b) shows the sequence inserted in adenovirus AdΔ24RGD replacing the sequence from nucleotides 419 to 422. This insertion is made to insert four binding sites to factor E2F-1 and one binding site to Sp1 factor. The sequences underlined as "nt 385-419" and "nt 422-461" corresponds to the wild type of AdΔ24RGD. (c) shows the complete cassette inserted in the genomes of ICOVIR17 and AdwtRGD-PH20 with respect to the genomes of ICOVIR15 and AdwtRGD (SEQ ID NO: 4). The splicing acceptor IIIa, kozak, and polyadenylation (polyA) sequences are indicated. Protein PH20 encoding sequence spans from the kozak to the polyadenylation sequence.

FIG. 2 shows the amino acid sequence of the PH20 protein (SEQ ID NO: 1) and a hydropathic plot according to the algorithm of Kyte-Doolittle. Protein PH20 is a membrane protein present in the plasmatic and acrosomal membranes of the spermatozoa. (a) The amino acid sequence shows the hydrophobic sequence responsible for the anchorage of the protein in the membrane (sequence underlined). In the present invention, the PH20 protein expressed by the virus presents a deleted hydrophobic tail. The cut point is indicated inside a circle. By means of this deletion protein PH20 is secreted to the extracellular medium. (b) Hydropathic plot of the terminal 100 amino acids of PH20 protein according to Kyte-Doolittle. The arrow indicates the beginning of the hydrophobic that has been eliminated.

FIG. 3 corresponds to EXAMPLE 4.

FIG. 4 demonstrates that the insertion and expression of the hyaluronidase PH20 gene does not interfere with the replication of a tumour-selective replicating-adenovirus. Cells from cell lines A549 (a) and SKMel28 (b) were infected with oncolytic adenoviruses ICOVIR15 and ICOVIR17 (that differs from ICOVIR15 by containing the PH20 gene) and the amount of virus in the cell extracts was measured (total virus, X-axis, in TU/ml) at different times (Y-axis, in hours post-infection). The graphs show that the kinetics of virus production is identical for both viruses, demonstrating that the insertion and expression of the hyaluronidase PH20 gene, in adenovirus ICOVIR17, does not affect virus replication. FIG. 4 corresponds to EXAMPLE 5.

FIG. 5 shows the oncolytic efficacy in vitro of an oncolytic adenovirus that contains and expresses the hyaluronidase PH20 gene. The oncolytic activity of an adenovirus expressing hyaluronidase PH20 (ICOVIR17) was compared in vitro to the activity of a similar oncolytic virus without the hyaluronidase PH20 gene (ICOVIR15) in two tumour cell lines expressing a high amount of hyaluronic acid, SKMel28 (a) and PC3 (b). The cytopathic effect (CPE) that the virus induces is measured as a decrease in protein levels in an infected cell monolayer (measured with the BCA method). Cells were seeded in 96-well plates at 10000 cells/well. On the following day, cells were infected with serial dilutions of the virus. Infected cells were incubated during 5 days, washed with PBS, and the amount of protein remaining in the well was measured. The results show that in vitro the expression of hyaluronidase PH20 does not improve the oncolytic activity of the adenovirus, as the cytotoxicity curves were the same for both viruses. The % of cellular survival against TU/cell is plotted. FIG. 5 corresponds to EXAMPLE 5.

FIG. 6 demonstrates the antitumour activity of an oncolytic adenovirus expressing hyaluronidase PH20 in vivo. Human melanoma cells (SKMel28) were inoculated at each flank of Balb/c athymic mice. Once the tumours reached an average size of 150 mm3, they were injected with PBS or $1 \times 10^8$ transducing units of AdwtRGD-PH20 (10 tumours/group). (a) The graph shows the average tumour growth (in %) in each group with respect to day 0 as a function of time post-administration (in days). The result demonstrates that the oncolytic adenovirus expressing the hyaluronidase PH20 gene has a higher antitumour activity, statistically significant compared to the control group (PBS), p<0.00001. The 100% of the tumours injected with AdwtRGD-PH20 had regressed between a 10% and a 50% of volume at day 27 post-injection, as opposed to a 0% regression in the group injected with PBS. (b) The amount of hyaluronic acid in the tumours injected with PBS or AdwtRGD-PH20 was analyzed at the end of the experiment by immunohystochemistry. The images show that the tumours injected with AdwtRGD-PH20 have a lower amount of hyaluronic acid compared to the control tumours. FIG. 6 corresponds to EXAMPLE 6.1.

FIG. 7 corresponds to EXAMPLE 6.2.

FIG. 8 shows that the expression of hyaluronidase PH20 improves the antitumour effect of an oncolytic adenovirus after its systemic administration. Human melanoma cells (SKMel28) were inoculated in each back flank of Balb/c athymic mice. Once the tumours reached an average of 100 mm3, the mice were injected with PBS or $5\times10^{10}$ physical particles of ICOVIR15 or ICOVIR17 (ICOVIR15 armed with PH20) (8-10 tumours/group) endovenously. (a) The graph shows the average tumour growth (in %) of each group with respect to day 0 as a function of the time post-administration (in days). The result demonstrates that the expression of hyaluronidase PH20 results in an increase of the oncolytic potency of adenovirus, as the suppression of the tumour growth induced by ICOVIR17 is significantly higher than the suppression induced in the group control (ICOVIR15), *p<0.00001. (b) The images show the distribution of adenovirus ICOVIR15 and ICOVIR17 within the tumours extracted at the end of the experiment (day 48). The tumours of mice injected with the oncolytic adenovirus ICOVIR17 show very extensive necrotic areas (heavy arrow), a reduced number of areas with viable cells (v), and large and numerous centres of viral replication (areas with green fluorescence indicated with thin arrows) in comparison with the tumours injected with the adenovirus control, ICOVIR15. FIG. 8 corresponds to EXAMPLE 6.3.

FIG. 9 demonstrates that the increase of antitumour systemic activity of adenoviruses expressing the enzyme hyaluronidase PH20 is not restricted to one tumour type. (a) The graph shows the average growth of pancreatic tumours NP-18 (in %) for each group with respect to day 0 as a function the time post-administration (in days). #, means significant (p≤0.02) compared to the tumours treated with PBS from day 14 to 30; &, significant (p≤0.05) compared to the tumours treated with PBS from day 14 to 30; *, significant (p≤0.02) compared to the tumours treated with ICOVIR-15 from day 12 to 30. (b) The images show the distribution of adenovirus ICOVIR15 and ICOVIR17 in tumours NP-18 at day 30. *, p≤0.01 compared to the tumours treated with ICOVIR15. "% p.a." means % of positive area. FIG. 9 corresponds to EXAMPLE 6.4.

FIG. 10 (a) shows the structure of oncolytic adenoviruses ICOVIR17 and ICOVIR17RGDK. (b) shows the amino acid sequence of the modified version of the fibre in ICOVIR17RGDK. The underlined sequence corresponds to the amino acids 91RGDK94 that are different with respect to the wild type form of the human adenovirus type 5 fibre. FIG. 10 corresponds to EXAMPLE 8.

FIG. 11 shows the oncolytic activity of two adenoviruses (ICOVIR17 and ICOVIR17RGDK) in two tumour cell lines, one of lung adenocarcinoma A549 (a) and another one of pancreatic adenocarcinoma NP-18 (b). % of cell survival versus TU/cell. FIG. 11 corresponds to EXAMPLE 9.

EXAMPLES

Figure 1:
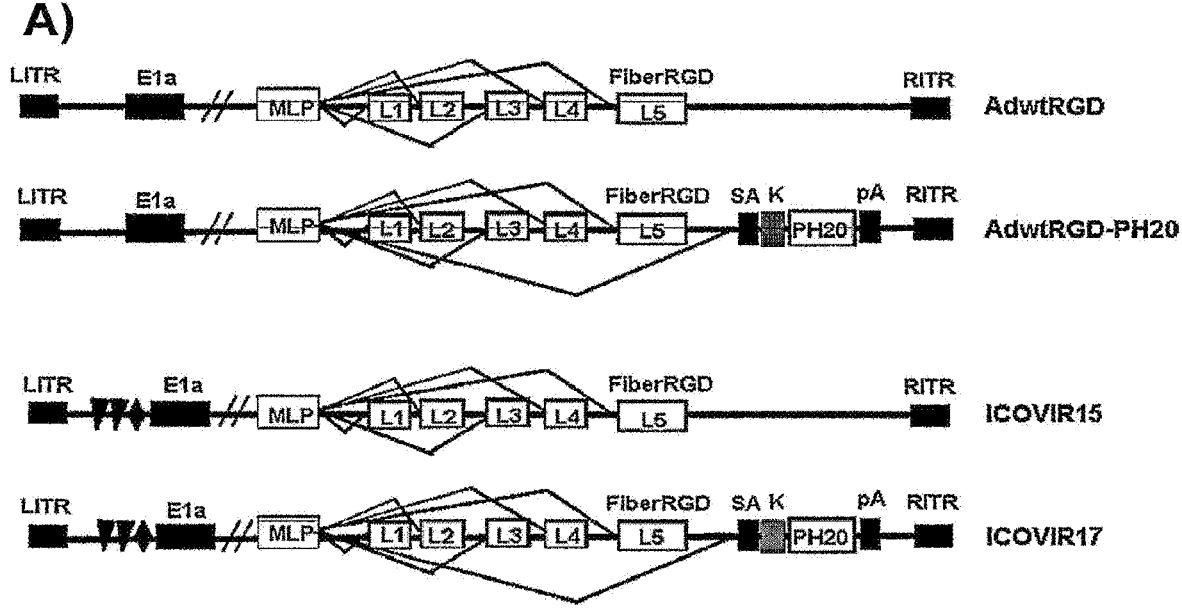
FIG. 1 relates to EXAMPLE 3.

Example 1. Construction of the Oncolytic Adenoviruses

Two oncolytic adenoviruses containing the hyaluronidase PH20 gene were constructed: adenoviruses AdwtRGD-PH20 and ICOVIR17.

The cDNA of hyaluronidase PH20 was obtained by PCR amplification of the different exons using as a template the A549 cell line genome, followed by joining these exons with specific flanking primers that contain the MfeI restriction site. The resulting fragment was digested with MfeI and cloned by ligation in the shuttle plasmid, pNKFiberRGD (that contains the sequence of the adenovirus fibre modified with RGD), to produce plasmid pNKFiberPH20. The cDNA corresponding to PH20 cloned in plasmid pNKFiberPH20 is in SEQ ID NO: 2. The SEQ ID NO: 2 shows the codifying nucleotides for protein PH20 (isoform with GenBank access number NP_694859.1) from the start codon (ATG) to position 1467. The nucleotide sequence from region 1468 to the 1527 of this GenBank sequence codifies for the hydrophobic tail of the protein that anchors the protein to the membrane. This sequence has been deleted and it does not appear in SEQ ID NO: 2. After nucleotide 1468 the translation termination codon TAA has been added.

Example 2. Construction of AdwtRGD-PH20 Adenovirus

In order to generate adenovirus AdwtRGD-PH20, the gene of the adenoviral fibre of plasmid pVK50cau (that contains the complete sequence of the Ad5 with a Swa I restriction site in the fibre) was replaced using homologous recombination in yeast by the fibre gene followed by the hyaluronidase PH20 gene obtained from plasmid pNKFiberPH20 digested with NotI/KpnI.

The adenovirus AdwtRGD-PH20, characterized by expressing the hyaluronidase PH20 gene under the control of the major late promoter, and by containing the tri-peptide RGD in the adenoviral fibre, was generated by digestion with Pac I of plasmid pAdwtRGD-PH20 and transfection in HEK293 cells. The adenovirus AdwtRGD, previously described, is characterized by containing the tri-peptide RGD in the adenoviral fibre (cfr. M. Majem et al., "Control of E1A to under an E2F-1 to promoter insulated with the myotonic dystrophy locus insulator reduces the toxicity of oncolytic adenovirus Ad-Delta24RGD", *Cancer Gene Therapy* 2006, vol. 13, pp. 696-705). AdwtRGD was constructed by digestion of plasmid pVK503 that contains the complete genome of Ad5 with the fibre modified with RGD (cfr. I. Dmitriev et al., "An adenovirus receiving-independent vector with genetically modified fibres demonstrates expanded tropism via utilization of a coxsackievirus and adenovirus cell entry mechanism", *J. Virol.* 1998, vol. 72, pp. 9706-13) with Pac I followed by transfection of 293 cells.

Example 3. Construction of Adenovirus ICOVIR17

In order to generate this adenovirus, the adenoviral plasmid pICOVIR17 was used. To generate this plasmid, the adenovirus fibre gene from plasmid pICOVIR15 was replaced by homologous recombination in yeast with the fibre gene followed by the hyaluronidase PH20 gene from plasmid pAdwtRGD-PH20 digested with SpeI/PacI.

Adenovirus ICOVIR15 derives from adenovirus AdΔ24RGD that is characterized by containing the Δ24 deletion in the E1a protein encoding sequence. This deletion affects the interaction of E1a with pRB. AdΔ24RGD has also the insertion of peptide RGD in the adenoviral fibre to increase the infectivity of the virus. These two modifications are described in K. Suzuki et al., "Conditionally replicative adenovirus with enhanced infectivity shows improved oncolytic potency", *Clin Cancer Res* 2001, vol. 7, pp. 120-6. From AdΔ24RGD, four E2F-1 binding sites and one Sp1 binding site were inserted in the endogenous E1a promoter to control the expression of E1a. In this way ICOVIR15 was obtained. This insertion was made by replacing the sequence 419-422 of the genome with the sequence with the 4 E2F-1 binding sites and one Sp1 binding site, so that the final sequence is the one that appears in the SEQ ID NO: 3 and FIG. 1(b). To perform this step, a unique BsiW I restriction site was created by directed mutagenesis in the E1A promoter of pEndK/Spe plasmid (cfr. J. E. Carette et al., "Conditionally replicating adenoviruses expressing short hairpin RNAs silence the expression of a target gene in cancer cells", *Cancer Res* 2004, vol. 64, pp. 2663-7). The Sp1 binding site was introduced in plasmid pEndK/Spe within the BsiW I site by ligating this BsiWI-cut plasmid with primers Sp1F (5'-GTACGTCGACCACAAACCCC GCCCAGCGTCTTGTCATTGGCGTCGACGCT-3' SEQ ID NO: 5) and Sp1R (5'-GTACAGCGTCGACGC-CAATGACAAGACGCTGGGCGGGGTTTGTGGT CGAC-3' SEQ ID NO: 6) hybridized to each other. The E2F binding sites were introduced using binding primers E2FF2 (5'-GTACGTCGGCGGCTCGTGG CTCTTTCGCGGCAAAAAGGAT- TTGGCGCGTAAAAGTGGTTCGAA-3' SEQ ID NO: 7) and E2FR2 (5'-GTACTTCGAACCACTTTTACGCGC-CAAATCC TTTTTGCCGCGAAAGAGC-CACGAGCCGCCGAC-3' SEQ ID NO: 8) hybridized to each other, to create plasmid pEndK415Sp1E2F2. Next, the sequence CAU that contains the necessary elements for plasmid replication in yeasts (a centromere, the autonomous replicating region ARS, and the selection marker URA3) was introduced by homologous recombination in yeast to create plasmid pEndK415Sp1E2F2CAU. Finally, a homologous recombination was made in yeasts between plasmid pEndK415Sp1E2F2CAU digested with KpnI and the adenovirus genome of adenovirus AdΔ24RGD to construct pICOVIR15cau. ICOVIR15 was obtained by transfection of the PacI-digested pICOVIR15cau into HEK293 cells.

The ICOVIR17 virus, that contains the same modifications as ICOVIR15 plus the insertion of the hyaluronidase gene behind the adenovirus fibre gene, was generated by digestion with PacI of plasmid pICOVIR17 and transfection into HEK293 cells. The correct structure of AdwtRGD-PH20 and ICOVIR17 genomes was verified by restriction with Hind III. In addition, the region of PH20 gene was sequenced with specific primers.

The complete cassette inserted in ICOVIR17 and AdwtRGD-PH20 genomes compared to ICOVIR15 and AdwtRGD genomes is shown in FIG. 1(c) and in SEQ ID NO: 4: The PH20 protein encoding sequence falls between the kozak sequence and the polyadenylation sequence.

Figure 3:
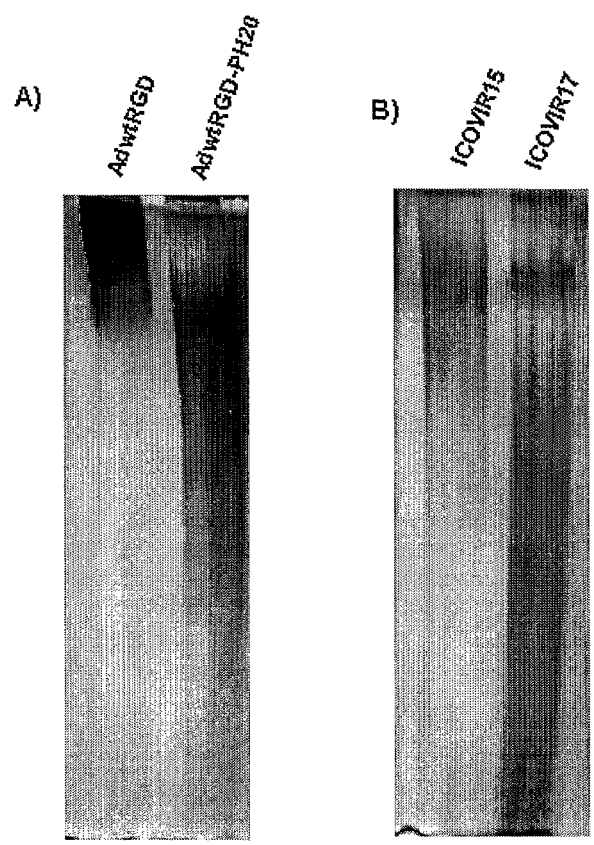
FIG. 3 demonstrates that oncolytic adenoviruses that contain the gene of hyaluronidase PH20 express a soluble protein that displays hyaluronidase activity. The gels show that hyaluronic acid samples incubated with the supernatant of the virus that express hyaluronidase PH20 have been digested producing oligosaccharides of different sizes. The samples incubated with the supernatants of the control adenoviruses (AdwtRGD and ICOVIR15) display non-digested hyaluronic acid.

Example 4. Expression of a Soluble Protein with Hyaluronidase Activity by an Adenovirus that Contains the Hyaluronidase PH20 Gene To demonstrate that an adenovirus that contains the hyaluronidase PH20 gene expresses a soluble protein with hyaluronidase activity, cultures of the A549 cell line were infected with viruses AdwtRGD, AdwtRGD-PH20, ICOVIR15, or ICOVIR17 using a multiplicity of infection that allowed more of 80% of infection (20 M.O. I). 24 h post-infection the infection medium was replaced with fresh medium. Then, after an additional 24 h, the fresh medium (or supernatant) was harvested and concentrated by filtration in a column of Amicon Extreme (Millipore, Billerica, the USA), according to the instructions of the manufacturer. The concentrated supernatants were incubated overnight at 37° C. with a hyaluronic acid solution (1.5 mg/ml) in phosphate buffer (pH=6) containing 0.1 M NaCl and 0.05% BSA. The digested hyaluronic acid was analyzed by electrophoresis in a 15% polyacrylamide gel (cfr. M. Ikegami-Kawai et al., "Microanalysis of hyaluronan oligosaccharides by polyacrylamide gel electrophoresis and its application to assay of hyaluronidase activity", *Analytical biochemistry* 2002, vol. 311, pp. 157-65). The oligosaccharides products of the hyaluronic acid digestion were fixed into the gel matrix in a solution of Alcian Blue during 30 min. Finally, the oligosaccharides were stained with silver nitrate. The result is shown in FIG. 3. The results demonstrate that the supernatant of cells infected with adenoviruses that contain the hyaluronidase PH20 gene (AdwtRGD-PH20 and ICOVIR17) contains a soluble protein able to digest hyaluronic acid (polysaccharide of elevated molecular weight) into oligosaccharides of 5 to more than 50 disaccharide repeat units.

Example 5. Absence of Effect in Virus Replication and In Vitro Cytotoxicity Mediated by the Oncolytic Adenovirus that Expresses the Hyaluronidase PH20 Gene To verify that the insertion of the hyaluronidase PH20 gene did not affect virus replication, A549 and SKMel-28 tumour cell lines were infected with oncolytic adenoviruses ICOVIR15 or ICOVIR17. Four hours post-infection the infection medium was replaced with fresh medium. Total cell extracts were harvested at different times post-infection and they were freeze-thawed three times to release the virus. The amount of virus in the cell extract was determined by infection of HEK293 and anti-hexon staining (cfr. M. Majem supra). The result is shown in FIG. 4. The insertion of the hyaluronidase PH20 gene does not affect the replication of adenovirus ICOVIR17, as this virus shows the same replication as the adenovirus control.

To demonstrate the effect of the hyaluronidase PH20 expression on the cytotoxicity of the oncolytic adenovirus in vitro, cells from PC3 and SKMel-28 tumour cell lines were infected with serial dilutions of viruses ICOVIR15 or ICOVIR17. Five and six days post-infection, respectively, the amount of protein, as an indicator of cell survival, was evaluated in a spectrophotometer. The results are shown in FIG. 5. The lytic activity of ICOVIR17 in these two tumour lines is the same as the activity of ICOVIR15, indicating that hyaluronidase PH20 expression does not offers any oncolytic advantage in vitro.

Example 6. Use of a Replicating Adenovirus that Contains the Hyaluronidase PH20 Gene to Treat Tumours Efficiently 6.1. An in vivo experiment was made using athymic mice of the Balb/c strain with engrafted SKMel-28 tumours. A total of $5 \times 10^6$ tumour cells of the SKMel-28 cell line were injected subcutaneously in each flank of the mouse. After 21 days, the mice with tumours (with a tumour volume of 150 mm3) were distributed in different experimental groups (n=10 by group). The tumours of the control group received a single intratumour injection of saline buffer (20 µl). The mice of the group treated with AdwtRGD-PH20 received a intratumour injection (20 µl) of $1 \times 10^8$ transducing units of this virus per tumour (equivalent to $2 \times 10^9$ virus particles or vp). The tumours were measured every two or three days with a caliper and the tumour volume was calculated according to the formula: V (mm$^3$)=A (mm)×B$^2$ (mm$^2$)×p/6, in where A it is the greater or longitudinal length, and B is the cross-sectional length. FIG. 6 shows the percentage of tumour growth relative to the beginning of the treatment (day 0). The results are shown as the average±S.E. The statistical significance of the differences between the results was calculated using a non-parametric Mann-Whitney test for non-matched data. The growth curves were compared using a variance analysis. The results were considered significant if p<0.05. The treatment of the tumours with adenovirus AdwtRGD-PH20 yielded tumour regressions in 100% of the treated tumours. The % of tumour growth was significantly smaller compared to the control group since the first days post-injection. The analysis of the tumours at the end of the experiment showed a reduction in the amount of hyaluronic acid present in the extracellular matrix of the tumours injected with AdwtRGD-PH20.

Figure 7:
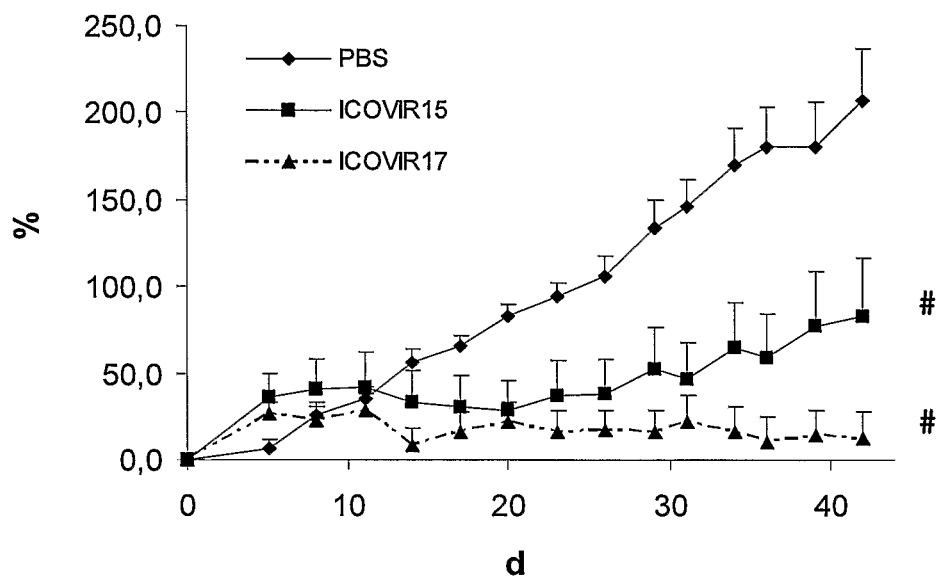
FIG. 7 shows that the expression of hyaluronidase PH20 improves the antitumour effect of an oncolytic adenovirus after its intratumour administration. Human melanoma cells (SKMel28) were inoculated in each back flank of Balb/c athymic mice. Once the tumours reached an average volume of 130 mm3, they were injected with PBS or $1\times10^8$ transducing units of ICOVIR15 or ICOVIR17 (10 tumours/group) in an single dose. (a) The graph shows the average growth of the tumours (in %) with respect to day 0 as a function of time post-administration (in days). The oncolytic adenovirus that expresses hyaluronidase PH20 (ICOVIR17) presents a better antitumoural effect than the control adenovirus that does not express this hyaluronidase (ICOVIR15). (b) After 42 days of treatment, the mice were sacrificed and the tumours were harvested and weighted. The table shows a summary of the tumour volume, percentage of tumour growth, and weight of the tumours at the end of the experiment. The tumours injected with ICOVIR17 present a significantly lower tumour weight compared to the tumours injected with ICOVIR15 (*p<0.05) and to the tumours injected with PBS (# p<0.05). Unlike the results obtained in vitro, where the virus can spread without difficulty through the cell monolayer, the results in vivo demonstrate that inside a tumour, where the extracellular matrix opposes to the spread of the virus, the expression of hyaluronidase PH20 increases the antitumour potency of an oncolytic adenovirus.

6.2. In another experiment, the treatment was performed by intratumoural injection of ICOVIR15 or ICOVIR17. Tumours of the human melanoma cell line SKMel-28 were implanted in athymic mice Balb/C nu/nu and, once established, they were treated intratumorally with PBS or $1 \times 10^8$ transducing units of viruses ICOVIR15 or ICOVIR17 (equivalent to $2 \times 10^9$ virus particles or vp). The results are shown in FIG. 7. Treatment with ICOVIR17 showed an oncolytic activity that resulted in a tumour growth inhibition significantly different to the control group (PBS), p<0.05. At the end of the experiment tumours were excised and weighted. The table of FIG. 7 shows the averages of tumour volume, percentage of tumour growth, and weight of the tumours at the end of the experiment. The weight of the tumours injected with ICOVIR17 is significantly lower to the weight of the tumours in the control groups, PBS (# p<0.05) and ICOVIR15 (*p<0.05).

6.3. In another experiment the treatment was performed by systemic injection of ICOVIR15 or ICOVIR17. Tumours of the human melanoma cell line SKMel-28 were implanted in athymic Balb/C nu/nu mice and, once established, animals were treated via tail vein injection with PBS or $5 \times 10^{10}$ physical particles of virus ICOVIR15 or ICOVIR17. The results are shown in FIG. 8. Treatment with ICOVIR17 demonstrated an oncolytic activity that resulted in a tumour growth suppression significantly different from the control groups, PBS (# p<0.0001) and ICOVIR15 (*p<0.00001). At the end of the experiment, the tumours were excised and frozen in OCT. Different sections from the tumours frozen in OCT were treated with an α-hexon antibody (adenovirus capsid protein) and were counterstained with 4',6-diamidino-2-phenylindole. The antitumour activity of ICOVIR17 correlates with the replication of adenovirus at the intratumoural level, which was evaluated in the tumours obtained at day 48 post-injection. The tumours treated with ICOVIR17 show large necrotic areas, a better viral distribution, and fewer areas of viable cells than the tumours injected with ICOVIR15.

6.4. In another experiment the treatment was performed by systemic injection of ICOVIR15 or ICOVIR17 in Balb/C athymic nu/nu mice implanted with tumours from the human pancreatic adenocarcinoma cell line NP-18. Once tumours were established, reaching an average volume of 60 mm3, the animals were treated via tail vein with PBS or $5 \times 10^{10}$ physical particles of viruses ICOVIR15 or ICOVIR17 (10 tumours/group). The results are shown in FIG. 9, where it is demonstrated that the increase of antitumour activity of an adenovirus expressing the hyaluronidase PH20 enzyme is not restricted to a single tumour type.

FIG. 9(a) demonstrates that hyaluronidase PH20 expression results also in an increase of the oncolytic potency of adenovirus, compared to the PBS group and to the virus control group (ICOVIR15). # means significant (p≤0.02) compared with the tumours treated with PBS from days 14 to 30. & means significant (p≤0.05) compared with the tumours treated with PBS from days 14 to 30. * means significant (p≤0.02) compared with the tumours treated with ICOVIR15 from day 12 to 30. At day 30, the tumours were excised and frozen in OCT, and later treated with a α-hexon antibody and counterstained with DAPI.

To quantify the level of intratumoural replication of ICOVIR-17, five viable areas of each tumour were analyzed (7/10 animals by group) for anti-hexon staining and the positive area percentage was measured by computerized image analysis (software ImageJ). The results of this analysis are shown in FIG. 9(b) where it is noted that NP-18 tumours treated with ICOVIR17 display a significantly larger area of adenovirus staining compared to the tumours treated with ICOVIR15 (*, significant p≤0.01).

Example 7. Toxicology Profile of Oncolytic Adenoviruses Expressing the Hyaluronidase Gene To verify that the insertion of the hyaluronidase gene does not modify substantially the pattern of toxicity induced by oncolytic adenoviruses upon endovenous administration, Syrian hamsters (*Mesocricetus auratus*) were used, as this is an animal model permissive to human adenovirus replication. Hamsters constitute an animal model permissive to the replication of human adenovirus. Female, immune competent, 5 week-old animals were used (5-6 animals/group).

They received a single dose of 4×10$^{11}$ vp of ICOVIR15 or ICOVIR17 intravenously through the cephalic vein at day 0 in 300 µl of PBS. The control group was injected with the same volume of PBS. Five days post-administration, the animals were sacrificed and total blood and serum were obtained from each one by cardiac puncture to measure parameters of hepatic toxicity (AST and ALT enzymes) and to count the different blood cell populations by flow cytometry (hemogram). Simultaneously, the livers of the animals were obtained and fixed in 4% paraformaldehyde for haematoxylin/eosin staining.

The results of the hepatic toxicity study indicated that both viruses induce a certain degree of hepatic inflammation in this model, with an elevation of AST and ALT transaminase levels. However, no differences were observed between the animals treated with ICOVIR15 or ICOVIR17. At haematological level, both viruses caused elevations of the populations of neutrophils, basophils, and monocytes, as well as reduced platelet counts with respect to the control animals, but again without differences between ICOVIR15 and ICOVIR17.

Example 8. Construction of Virus ICOVIR17RGDK

To generate this adenovirus, adenoviral plasmid pICOVIR17RGDK was used. In this plasmid the fibre gene of wild type adenovirus 5 has been replaced with a version modified in its heparan-sulfate binding domain (amino acids 91KKTK94 of the polypeptide sequence replaced with 91RGDK94). The pICOVIR17RGDK plasmid was constructed by an homologous recombination in yeasts between the NdeI partial digestion product of pICOVIR17 and the EcoRI-digested pBSattKKT plasmid (that contains the modified version of the adenovirus fibre as described in N. Bayo et al. "Replacement of adenovirus type 5 fibre shaft heparan sulphate proteoglycan-binding domain with RGD for improved tumour infectivity and targeting". *Human Gene Therapy* 2009, vol. 20, pp 1214-21).

FIG. 10 shows the position of the modification 91RGDK94 in the context of ICOVIR17RGDK, as well as the complete sequence of the fibre protein in this adenovirus. Adenovirus ICOVIR17 contains a version of the adenovirus fibre gene where peptide RGD-4C (Cys-Asp-Cys-Arg-Gly-Asp-Cys-Phe-Cys has been inserted; CDCRGDCFC, SEQ ID NO: 10) in HI-loop of the knob domain of the protein (a hypervariable loop non-conserved evolutionarily and very exposed in the adenovirus capsid). ICOVIR17RGDK is totally analogous to ICOVIR17 except in the fibre gene, as the ICOVIR17RGDK fibre only differs from the wild type human adenovirus type 5 in the replacement of amino acids $^{91}$KKTK$^{94}$ (SEQ ID NO: 11) with the high affinity integrin-binding peptide $^{91}$RGDK$^{94}$ (SEQ ID NO: 12) in the shaft domain of the protein (SEQ ID NO: 9).

Example 9. Oncolytic Efficacy of the Adenovirus with the Capsid Modification ICOVIR17RGDK As shown in FIG. 11, the capsid modification present in ICOVIR17RGDK does not alter the in vitro cytotoxicity of an oncolytic adenovirus that contains and expresses the hyaluronidase PH20 gene. The oncolytic activity of two adenoviruses that express hyaluronidase PH20 (ICOVIR17 and ICOVR17RGDK) were compared in two tumour cell lines, A549 derived from lung adenocarcinoma (FIG. 11(*a*)) and NP-18 derived from pancreatic adenocarcinoma (FIG. 11(*b*)). The cytopathic effect induced by the virus is measured as a decrease of the protein amount in an infected cellular monolayer (BCA method). The cells of the two tumour cell lines were seeded in 96-well plates at 10000 cells/well. At the next day the cells were infected with serial dilutions of virus. Infected cells were incubated during 6 days, washed with PBS, and the amount of protein remaining in the well was measured. The results show that in vitro, the capsid modification does not change significantly the oncolytic activity of adenoviruses.

Example 10. Different Toxicology Profile of Oncolytic Adenoviruses that Express the Hyaluronidase Gene To evaluate the impact of the RGDK modification in the background of oncolytic adenoviruses expressing hyaluronidase, immune-competent Balb/C mice without tumours were used. Six week-old males were used (7 animals/group). They received a single dose of 5×10$^{10}$ vp of ICOVIR17 or ICOVIR17RGDK intravenously via tail vein at day 0 in 150 µl of PBS. At day 7 (2 animals/group) and day 12 (5 animals/group) post-administration, the animals were sacrificed and total blood and serum were obtained from each one by cardiac puncture to count the different blood cell populations by flow cytometry (hemogram) and to measure parameters of hepatic toxicity (AST and ALT enzymes). The result of this study showed that both viruses increased the levels of enzymes at day 7. However these levels return to normal values at day 12. No significant differences are observed between the ICOVIR17 and ICOVIR17RGDK groups, although a lower hepatotoxicity trend was observed in the group of animals injected with ICOVIR17RGDK compared to the ICOVIR17 group (slightly lower levels of AST and ALT). With regard to the haematological profile of the animals at day 12 post-administration, no significant differences were observed in white blood cells and platelet counts, except for the number of lymphocytes that was lower in animals treated with ICOVIR17 than in animals PBS and ICOVIR17RGDK groups.

SEQUENCE LISTING

```
<160> NUMBER OF SEQ ID NOS: 12

<210> SEQ ID NO 1
<211> LENGTH: 509
<212> TYPE: PRT
<213> ORGANISM: Homo sapiens

<400> SEQUENCE: 1

Met Gly Val Leu Lys Phe Lys His Ile Phe Phe Arg Ser Phe Val Lys
1               5                   10                  15
```

```
Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
50                      55                  60

Asp Glu Pro Leu Asp Met Ser Leu Phe Ser Phe Ile Gly Ser Pro Arg
65                      70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
130                     135                 140

Ile Asp Trp Glu Glu Trp Arg Pro Thr Trp Ala Arg Asn Trp Lys Pro
145                     150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
210                     215                 220

Tyr Asn His His Tyr Lys Lys Pro Gly Tyr Asn Gly Ser Cys Phe Asn
225                     230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
290                     295                 300

Arg Ile Val Phe Thr Asp Gln Val Leu Lys Phe Leu Ser Gln Asp Glu
305                     310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
370                     375                 380

Gly Val Cys Ile Arg Lys Asn Trp Asn Ser Ser Asp Tyr Leu His Leu
385                     390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430
```

```
Phe Tyr Cys Ser Cys Tyr Ser Thr Leu Ser Cys Lys Glu Lys Ala Asp
            435                 440                 445
Val Lys Asp Thr Asp Ala Val Asp Val Cys Ile Ala Asp Gly Val Cys
450                 455                 460
Ile Asp Ala Phe Leu Lys Pro Pro Met Glu Thr Glu Pro Gln Ile
465                 470                 475                 480
Phe Tyr Asn Ala Ser Pro Ser Thr Leu Ser Ala Thr Met Phe Ile Val
                485                 490                 495
Ser Ile Leu Phe Leu Ile Ile Ser Ser Val Ala Ser Leu
            500                 505
```

<210> SEQ ID NO 2
<211> LENGTH: 1473
<212> TYPE: DNA
<213> ORGANISM: Artificial Sequence
<220> FEATURE:
<223> OTHER INFORMATION: cDNA of the PH20 protein from the transcription
      start (ATG) to position 1467. The hydrofobic tail of the protein
      (nucleotides 1468-1527) has been deleted and it is not shown. The
      stop codon (TAA) has been added at the end.

<400> SEQUENCE: 2

```
atgggagtgc taaaattcaa gcacatcttt ttcagaagct tgttaaatc aagtggagta      60
tcccagatag ttttcacctt ccttctgatt ccatgttgct tgactctgaa tttcagagca    120
cctcctgtta ttcaaatgt gcctttcctc tgggcctgga atgccccaag tgaattttgt    180
cttggaaaat tgatgagcc actagatatg agcctcttct ctttcatagg aagcccccga    240
ataaacgcca ccgggcaagg tgttacaata ttttatgttg atagcttgg ctactatcct    300
tacatagatt caatcacagg agtaactgtg aatggaggaa tcccccagaa gatttcctta    360
caagaccatc tggacaaagc taagaaagac attacatttt atatgccagt agacaatttg    420
ggaatggctg ttattgactg gaagaatgg agacccactt gggcaagaaa ctggaaacct    480
aaagatgttt acaagaatag gtctattgaa ttggttcagc aacaaaatgt acaacttagt    540
ctcacagagg ccactgagaa agcaaaacaa gaatttgaaa aggcagggaa ggatttcctg    600
gtagagacta taaaattggg aaaattactt cggccaaatc acttgtgggg ttattatctt    660
tttccggatt gttacaacca tcactataag aaacccggtt acaatggaag ttgcttcaat    720
gtagaaataa aagaaatga tgatctcagc tggttgtgga atgaaagcac tgctctttac    780
ccatccattt atttgaacac tcagcagtct cctgtagctg ctacactcta tgtgcgcaat    840
cgagttcggg aagccatcag agtttccaaa ataccctgatg caaaaagtcc acttccggtt    900
tttgcatata cccgcatagt ttttactgat caagttttga aattcctttc tcaagatgaa    960
cttgtgtata catttggcga aactgttgct ctgggtgctt ctggaattgt aatatgggga   1020
accctcagta atgcgaagt atgaaatct tgcttgctcc tagacaatta catggagact   1080
atactgaatc cttacataat caacgtcaca ctagcagcca aatgtgtag ccaagtgctt   1140
tgccaggagc aaggagtgtg tataaggaaa aactggaatt caagtgacta tcttcaccct   1200
aacccagata attttgctat tcaacttgag aaaggtggaa agttcacagt acgtggaaaa   1260
ccgacacttg aagacctgga gcaatttct gaaaaatttt attgcagctg ttatagcacc   1320
ttgagttgta aggagaaagc tgatgtaaaa gacactgatg ctgttgatgt gtgtattgct   1380
gatggtgtct gtatagatgc tttttctaaaa cctcccatgg agacagaaga acctcaaatt   1440
ttctacaatg cttcaccctc cacactatct taa                                1473
```

<210> SEQ ID NO 3
<211> LENGTH: 246
<212> TYPE: DNA
<213> ORGANISM: Artificial Sequence
<220> FEATURE:
<223> OTHER INFORMATION: Sequence incorporated into Addelta24RGD
      adenovirus replacing its sequence from nucleotide 419 to 422. The
      first nucleotides 1-30 and the last 208-246 are from the wildtype
      Addelta24RGD.

<400> SEQUENCE: 3

```
ccaggtgttt ttctcaggtg ttttccgcgt actcggcggc tcgtggctct ttcgcggcaa    60
aaaggatttg gcgcgtaaaa gtggttcgaa gtactcggcg gctcgtggct ctttcgcggc   120
aaaaaggatt tggcgcgtaa aagtggttcg aagtacgtcg accacaaacc ccgcccagcg   180
tcttgtcatt ggcgtcgacg ctgtacgggg tcaaagttgg cgttttatta ttatagtcag   240
ctgacg                                                              246
```

<210> SEQ ID NO 4
<211> LENGTH: 1508
<212> TYPE: DNA
<213> ORGANISM: Artificial Sequence
<220> FEATURE:
<223> OTHER INFORMATION: Complete cassette integrated into the genomes
      of ICOVIR17 and AdwtRGD-PH20 with respect to genomes ICOVIR15 and
      AdwtRGD.

<400> SEQUENCE: 4

```
tactaagcgg tgatgtttct gatcagccac catgggagtg ctaaaattca agcacatctt    60
tttcagaagc tttgttaaat caagtggagt atcccagata gttttcacct tccttctgat   120
tccatgttgc ttgactctga atttcagagc acctcctgtt attccaaatg tgcctttcct   180
ctgggcctgg aatgccccaa gtgaattttg tcttggaaaa tttgatgagc cactagatat   240
gagcctcttc tctttcatag gaagccccg aataaacgcc accgggcaag gtgttacaat   300
attttatgtt gatagacttg gctactatcc ttacatagat tcaatcacag gagtaactgt   360
gaatggagga atcccccaga gatttccttt acaagaccat ctggacaaag ctaagaaaga   420
cattacattt tatatgccag tagacaattt gggaatggcc gttattgact gggaagaatg   480
gagacccact tgggcaagaa actggaaacc taaagatgtt tacaagaata ggtctattga   540
attggttcag caacaaaatg tacaacttag tctcacagag gccactgaga aagcaaaaca   600
agaatttgaa aaggcaggga aggatttcct ggtagagact ataaaattgg gaaaattact   660
tcggccaaat cacttgtggg gttattatct ttttccggat tgttacaacc atcactataa   720
gaaacccggt tacaatggaa gttgcttcaa tgtagaaata aaagaaatg atgatctcag   780 ctggttgtgg aatgaaagca ctgctcttta cccatccatt tatttgaaca ctcagcagtc   840
tcctgtagct gctacactct atgtgcgcaa tcgagttcgg gaagccatca gagtttccaa   900
aatacctgat gcaaaaagtc cacttccggt ttttgcatat acccgcatag ttttactga   960 tcaagttttg aaattccttt ctcaagatga acttgtgtat acatttggcg aaactgttgc  1020
tctgggtgct tctggaattg taatatgggg aaccctcagt ataatgcgaa gtatgaaatc  1080
ttgcttgctc ctagacaatt acatggagac tatactgaat ccttacataa tcaacgtcac  1140
actagcagcc aaaatgtgta gccaagtgct tgccaggag caaggagtgt gtataaggaa  1200
aaactggaat tcaagtgact atcttcacct caacccagat aattttgcta ttcaacttga  1260
gaaaggtgga agttcacag tacgtggaaa accgacactt gaagacctgg agcaattttc  1320
tgaaaaattt tattgcagct gttatagcac cttgagttgt aaggagaaag ctgatgtaaa  1380
```

```
agacactgat gctgttgatg tgtgtattgc tgatggtgtc tgtatagatg cttttctaaa    1440
acctcccatg gagacagaag aacctcaaat tttctacaat gcttcaccct ccacactatc    1500
ttaataaa                                                             1508

<210> SEQ ID NO 5
<211> LENGTH: 50
<212> TYPE: DNA
<213> ORGANISM: Artificial Sequence
<220> FEATURE:
<223> OTHER INFORMATION: oligonucleotide Sp1F

<400> SEQUENCE: 5
gtacgtcgac cacaaacccc gcccagcgtc ttgtcattgg cgtcgacgct                50

<210> SEQ ID NO 6
<211> LENGTH: 50
<212> TYPE: DNA
<213> ORGANISM: Artificial Sequence
<220> FEATURE:
<223> OTHER INFORMATION: oligonucleotide Sp1R

<400> SEQUENCE: 6
gtacagcgtc gacgccaatg acaagacgct gggcggggtt tgtggtcgac                50

<210> SEQ ID NO 7
<211> LENGTH: 63
<212> TYPE: DNA
<213> ORGANISM: Artificial Sequence
<220> FEATURE:
<223> OTHER INFORMATION: oligonucleotide E2FF2

<400> SEQUENCE: 7
gtacgtcggc ggctcgtggc tctttcgcgg caaaaaggat ttggcgcgta aaagtggttc    60
gaa                                                                   63

<210> SEQ ID NO 8
<211> LENGTH: 63
<212> TYPE: DNA
<213> ORGANISM: Artificial Sequence
<220> FEATURE:
<223> OTHER INFORMATION: oligonucleotide E2FR2

<400> SEQUENCE: 8
gtacttcgaa ccacttttac gcgccaaatc cttttttgccg cgaaagagcc acgagccgcc    60
gac                                                                   63

<210> SEQ ID NO 9
<211> LENGTH: 582
<212> TYPE: PRT
<213> ORGANISM: Artificial Sequence
<220> FEATURE:
<223> OTHER INFORMATION: Amino acid sequence, amino acids 1-582, of the
      modified version of the fibre in ICOVIR17RGDK

<400> SEQUENCE: 9

Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
            20                  25                  30

Phe Val Ser Pro Asn Gly Phe Gln Glu Ser Pro Pro Gly Val Leu Ser
        35                  40                  45
```

```
Leu Arg Leu Ser Glu Pro Leu Val Thr Ser Asn Gly Met Leu Ala Leu
 50                  55                  60

Lys Met Gly Asn Gly Leu Ser Leu Asp Glu Ala Gly Asn Leu Thr Ser
 65                  70                  75                  80

Gln Asn Val Thr Thr Val Ser Pro Pro Leu Arg Gly Asp Lys Ser Asn
                 85                  90                  95

Ile Asn Leu Glu Ile Ser Ala Pro Leu Thr Val Thr Ser Glu Ala Leu
                100                 105                 110

Thr Val Ala Ala Ala Ala Pro Leu Met Val Ala Gly Asn Thr Leu Thr
            115                 120                 125

Met Gly Ser Gln Ala Pro Leu Thr Val His Asp Ser Lys Leu Ser Ile
130                 135                 140

Ala Thr Gln Gly Pro Leu Thr Val Ser Glu Gly Lys Leu Ala Leu Gln
145                 150                 155                 160

Thr Ser Gly Pro Leu Thr Thr Asp Ser Ser Thr Leu Thr Ile Thr
                165                 170                 175

Ala Ser Pro Pro Leu Thr Thr Ala Thr Gly Ser Leu Gly Ile Asp Leu
            180                 185                 190

Lys Glu Pro Ile Tyr Thr Gln Asn Gly Lys Leu Gly Leu Lys Tyr Gly
            195                 200                 205

Ala Pro Leu His Val Thr Asp Asp Leu Asn Thr Leu Thr Val Ala Thr
210                 215                 220

Gly Pro Gly Val Thr Ile Asn Asn Thr Ser Leu Gly Thr Lys Val Thr
225                 230                 235                 240

Gly Ala Leu Gly Phe Asp Ser Gln Gly Asn Met Gln Leu Asn Val Ala
                245                 250                 255

Gly Gly Leu Arg Ile Asp Ser Gln Asn Arg Arg Leu Ile Leu Asp Val
            260                 265                 270

Ser Tyr Pro Phe Asp Ala Gln Asn Gln Leu Asn Leu Arg Leu Gly Gln
            275                 280                 285

Gly Pro Leu Phe Ile Asn Ser Ala His Asn Leu Asp Ile Asn Tyr Asn
            290                 295                 300

Lys Gly Leu Tyr Leu Phe Thr Ala Ser Asn Asn Ser Lys Lys Leu Glu
305                 310                 315                 320

Val Asn Leu Ser Thr Ala Lys Gly Leu Met Phe Asp Ala Thr Ala Ile
                325                 330                 335

Ala Ile Asn Ala Gly Asp Gly Leu Glu Phe Gly Ser Pro Asn Ala Pro
            340                 345                 350

Asn Thr Asn Pro Leu Lys Thr Lys Ile Ile Gly His Gly Leu Glu Phe
            355                 360                 365

Asp Ser Asn Lys Ala Met Val Pro Lys Leu Gly Thr Gly Leu Ser Phe
370                 375                 380

Asp Ser Thr Gly Ala Ile Thr Val Gly Asn Lys Asn Asn Asp Lys Leu
385                 390                 395                 400

Thr Leu Trp Thr Thr Pro Ala Pro Ser Pro Asn Cys Asp Leu Asn Ala
            405                 410                 415

Glu Lys Asp Ala Lys Leu Thr Leu Val Leu Thr Lys Cys Gly Ser Gln
            420                 425                 430

Ile Leu Ala Thr Val Ser Val Leu Ala Val Lys Gly Ser Leu Ala Pro
            435                 440                 445

Ile Ser Gly Thr Val Gln Ser Ala His Leu Ile Ile Arg Phe Asp Glu
            450                 455                 460

Asn Gly Val Leu Leu Asn Asn Ser Phe Leu Asp Pro Glu Tyr Trp Asn
```

```
                465              470              475              480
        Phe Arg Asn Gly Asp Leu Thr Glu Gly Thr Ala Tyr Thr Asn Ala Val
                        485              490              495

Gly Phe Met Pro Asn Leu Ser Ala Tyr Pro Lys Ser His Gly Lys Thr
                    500              505              510

Ala Lys Ser Asn Ile Val Ser Gln Val Tyr Leu Asn Gly Asp Lys Thr
                        515              520              525

Lys Pro Val Thr Leu Thr Ile Thr Leu Asn Gly Thr Gln Glu Thr Gly
                    530              535              540

Asp Thr Thr Pro Ser Ala Tyr Ser Met Ser Phe Ser Trp Asp Trp Ser
        545              550              555              560

Gly His Asn Tyr Ile Asn Glu Ile Phe Ala Thr Ser Ser Tyr Thr Phe
                        565              570              575

Ser Tyr Ile Ala Gln Glu
                    580

<210> SEQ ID NO 10
<211> LENGTH: 9
<212> TYPE: PRT
<213> ORGANISM: Artificial Sequence
<220> FEATURE:
<223> OTHER INFORMATION: peptide RGD-4C which is inserted into region HI
      of the adenoviral fibre

<400> SEQUENCE: 10

Cys Asp Cys Arg Gly Asp Cys Phe Cys
1               5

<210> SEQ ID NO 11
<211> LENGTH: 4
<212> TYPE: PRT
<213> ORGANISM: Artificial Sequence
<220> FEATURE:
<223> OTHER INFORMATION: Synthetic sequence

<400> SEQUENCE: 11

Lys Lys Thr Lys
1

<210> SEQ ID NO 12
<211> LENGTH: 4
<212> TYPE: PRT
<213> ORGANISM: Artificial Sequence
<220> FEATURE:
<223> OTHER INFORMATION: Synthetic sequence

<400> SEQUENCE: 12

Arg Gly Asp Lys
1
```

The invention claimed is:

1. A method for the treatment of a solid tumor in a subject, comprising administering a human oncolytic adenovirus to the subject, wherein the oncolytic adenovirus comprises a sequence encoding a human hyaluronidase enzyme inserted in the genome of the adenovirus, wherein:
- the human hyaluronidase amino acid sequence lacks a membrane binding domain resulting in a soluble enzyme;
- the expression of the hyaluronidase is controlled by a promoter;
- the adenovirus comprises a modified capsid comprising a replacement of the KKTK heparan sulfate proteoglycan binding sequence (SEQ ID NO: 11) with a RGDK sequence (SEQ ID NO: 12); and
- the solid tumor is characterized by selective replication of the adenovirus.

2. The method according to claim 1, wherein the human oncolytic adenovirus is selected from any of human adenovirus serotypes 1-51.

3. The method according to claim 2, wherein the human adenovirus is human adenovirus serotype 5.

4. The method according to claim 1, wherein the human hyaluronidase enzyme is human testicular hyaluronidase.

5. The method according to claim 1, wherein the hyaluronidase coding sequence is inserted into the genomic sequence of the oncolytic adenovirus downstream of the fibre coding sequence.

6. The method according to claim 1, wherein the promoter is selected from the group consisting of the cytomegalovirus promoter, the adenovirus major late promoter, the SV40 promoter, the herpes simplex virus thymidine kinase promoter, the RSV promoter, the EF1 alpha promoter, the beta-actin promoter, the human IL-2 promoter, the human IL-4 promoter, the IFN promoter, the E2F promoter, and the human GM-CSF promoter.

7. The method according to claim 1, wherein the adenovirus comprises a tissue-specific or a tumor-specific promoter, wherein the promoter controls the expression of one or more genes of the group of E1a, E1b, E2, and E4, to obtain selective replication in tumors.

8. The method according to claim 7, wherein the promoter is selected from the E2F promoter, the telomerase hTERT promoter, the tyrosinase promoter, the prostate-specific antigen promoter, the alphafetoprotein promoter, and the COX-2 promoter.

9. The method according to claim 1, wherein the adenovirus has mutations in one or more genes selected from E1a, E1b, E4, and VA-RNAs, to obtain selective replication in tumors.

10. The method according to claim 1, wherein the adenovirus comprises a sequence that optimizes the translation into protein of the sequence that encodes the hyaluronidase.

11. The method according to claim 1, wherein the adenovirus comprises a sequence selected from a splicing acceptor sequence, an IRES sequence, and a picornavirus 2A sequence.

12. The method according to claim 1, wherein the adenovirus comprises one or more genes inserted in its genome.

13. The method according to claim 1, wherein the solid tumor is a pancreatic cancer.

14. The method according to claim 1, wherein the solid tumor is a melanoma.

15. The method according to claim 1, wherein the adenovirus is administered directly to the tumor.

16. The method according to claim 1, wherein the adenovirus is administered systemically.

17. The method according to claim 1, wherein the solid tumor is a colon cancer.

18. The method according to claim 1, wherein the solid tumor is a lung cancer.

\* \* \* \* \*